United States Patent [19]

Morton, Jr.

[11] 3,997,566
[45] Dec. 14, 1976

[54] TRICYCLIC PROSTAGLANDIN

[75] Inventor: Douglas R. Morton, Jr., Portage, Mich.

[73] Assignee: The Upjohn Company, Kalamazoo, Mich.

[22] Filed: Aug. 13, 1975

[21] Appl. No.: 604,159

Related U.S. Application Data

[63] Continuation-in-part of Ser. No. 552,707, Feb. 24, 1975, abandoned, which is a continuation-in-part of Ser. No. 488,295, July 12, 1974, abandoned.

[52] U.S. Cl. ............ 260/340.7; 260/333; 260/340.9; 260/345.9; 260/347.8; 260/410.5; 260/448.2 B; 260/469; 260/473 A; 260/473 R; 260/479 R; 260/483; 260/484 R; 260/487
[51] Int. Cl.² .................................. C07D 319/06
[58] Field of Search ............. 260/340.7, 340.9

[56] References Cited
UNITED STATES PATENTS 3,873,570 3/1975 Kelly ........................... 260/340.7
3,879,423 4/1975 Kelly ........................... 260/340.7

Primary Examiner—Ethel G. Love
Attorney, Agent, or Firm—Morris L. Nielsen

[57] ABSTRACT

Process for preparing bicyclic diols of the formula

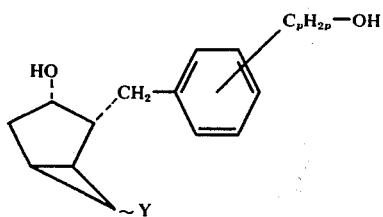

wherein $C_pH_{2p}$ is a valence bond or alkylene of one to 4 carbon atoms, inclusive, with one or 2 carbon atoms in the chain between the phenylene ring and —O—; wherein Y is a hydrocarbyl or substituted hydrocarbyl group; and wherein ~ indicates attachment to the cyclopropane ring in exo or endo configuration. These diols and the tricyclic prostaglandin intermediates prepared herein are useful intermediates in preparing prostaglandin analogs having pharmacological utility.

6 Claims, No Drawings

TRICYCLIC PROSTAGLANDIN INTERMEDIATES

CROSS REFERENCE TO RELATED APPLICATIONS

This application is a continuation-in-part of copending application Ser. No. 552,707 filed Feb. 24, 1975, now abandoned which was a continuation-in-part of co-pending application Ser. No. 488,295 filed July 12, 1974, now abandoned.

BACKGROUND OF THE INVENTION

This invention relates to intermediates useful in the preparation of prostaglandin analogs and to a process for preparing them.

Each of the known prostaglandins is a derivative of prostanoic acid which has the following structure and atom numbering:

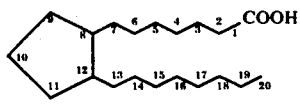

A systematic name for prostanoic acid is 7-[(2β-octyl)-cyclopent-1α-yl]heptanoic acid.

Prostaglandin $E_1$, "$PGE_1$", has the following structure:

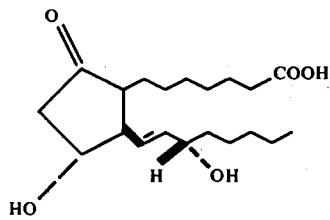

Prostaglandin $F_{1\alpha}$, "$PGF_{1\alpha}$", has the following structure:

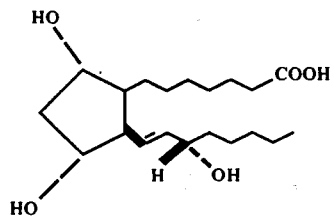

The prostaglandin formulas mentioned above each have several centers of asymmetry. Each formula represents a molecule of the particular optically active form of the prostaglandin obtained from certain mammalian tissues, for example, sheep vesicular glands, swine lung, and human seminal plasma, or by reduction or dehydration of a prostaglandin so obtained. See, for example, Bergstrom et al., Pharmacol. Rev. 20, 1 (1968), and references cited therein. The mirror image of each formula represents a molecule of the other enantiomeric form of that prostaglandin. The racemic form of the prostaglandins consists of equal numbers of two types of molecules, one represented by one of the above formulas and the other represented by the mirror image of that formula. Thus, both formulas are needed to define a racemic prostaglandin. See Nature 212, 38 (1966) for discussion of the stereochemistry of the prostaglandins.

In the formulas above, as well as in the formulas given hereinafter, broken line attachments to the cyclopentane ring indicate substituents in alpha configuration, i.e., below the plane of the cyclopentane ring. Heavy solid line attachments to the cyclopentane ring indicate substitutents in beta configuration, e.e., above the plane of the cyclopentane ring. In the formulas above, the hydroxyl attachment to carbon 15 is in the alpha configuration, as indicated by the broken line. In formulas below, this convention is also used for intermediates having hydroxyl substituted at the corresponding position on the side chain. A wavy line ~ indicates attachment to the side chain in alpha or beta configuration.

The various optically active and racemic prostaglandins and their alkyl esters are useful for various pharmacological purposes. With particular regard to $PGF_{1\alpha}$ see, for example, Bergstrom et al., Pharmacol. Rev. 20, 1 (1968), and references cited therein. As to the other prostaglandins, see, for example, Ramwell et al., Nature 221, 1251 (1969).

Previously, certain prostaglandin analogs having an oxa oxygen (—O—) and a divalent phenylene moiety

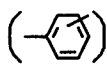

in the carboxyl-terminated side chain of the prostanoic acid structure (I) were disclosed. See German Offenlegungsschrift No. 2,209,990, Derwent Farmdoc No. 66750T.

Included among those phenylene-oxa prostaglandin analogs were compounds represented by the formulas:

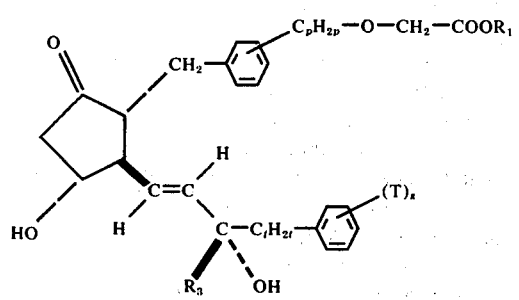

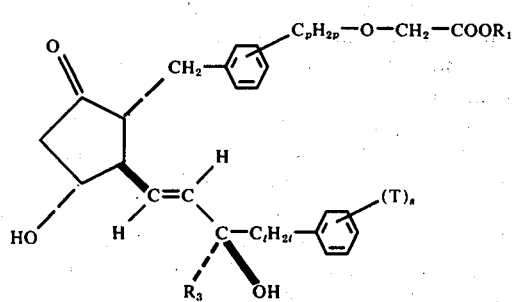

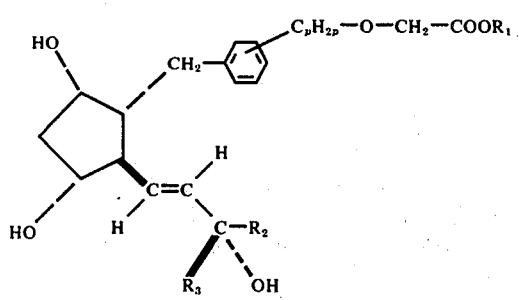

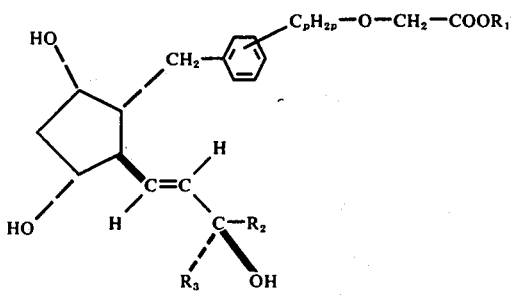

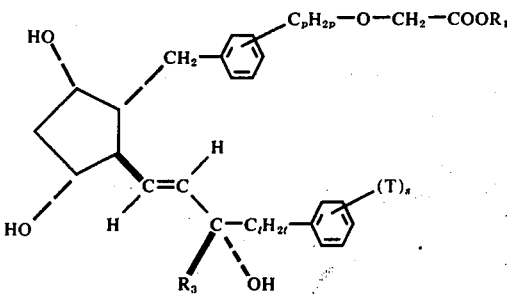

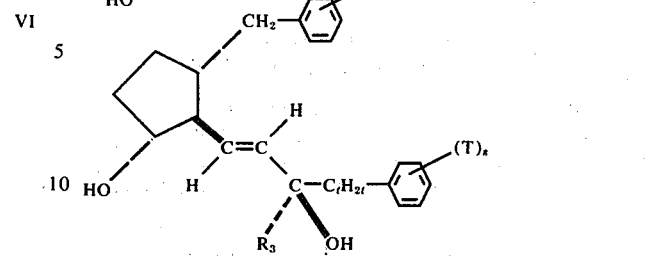

and the racemic mixtures of those compounds and their respective enantiomers represented by the mirror images of the above formulas. The terms $C_pH_{2p}$, $C_tH_{2t}$, $R_1$, $R_2$, and $R_3$, T, and s will be defined and illustrated below.

For example, specific compounds among the above phenylene-oxa prostaglandin analogs are represented by the following formulas by way of illustration:

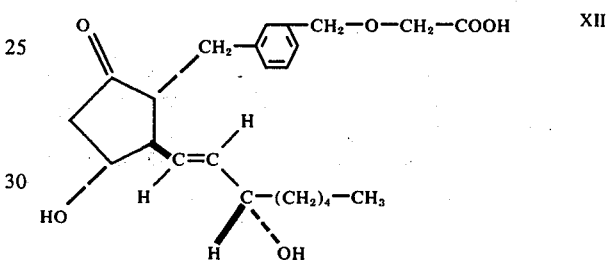

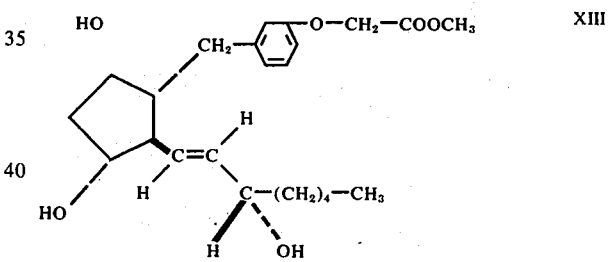

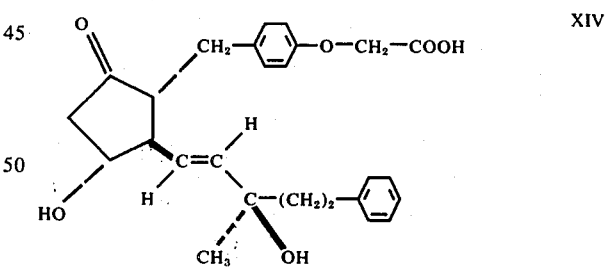

Based on its relationship to $PGE_1$ and prostanoic acid, the compound of formula XII is named 3-oxa-4,7-inter-m-phenylene-5,6-dinor-$PGE_1$. Similarly, the compound of formula XIII is named 3-oxa-3,7-inter-m-phenylene-4,5,6-trinor-$PGF_{1\alpha}$, methyl ester and the compound of formula XIV is named 3-oxa-3,7-inter-p-phenylene-15(R)-15-methyl-17-phenyl-4,5,6,18,19,20-hexanor-$PGE_1$.

These names for the compounds of formulas XII, XIII, and XIV are typical of the names of the phenylene-oxa prostaglandin analogs produced by the intermediates obtained by the novel process herein. These names are based on the structure and numbering system of prostanoic acid (formula I, above). That formula has seven carbon atoms in the carboxy-terminated chain and eight carbon atoms in the hydroxy-containing chain. In these names, "3-oxa" indicates an oxa oxygen (—O—) in place of the C-3 methylene of the prostaglandin (PG) compound.

The use of "nor", "dinor", "trinor", "tetranor", "pentanor", "hexanor", and the like in the names for the PG analogs referred to herein indicates the absence of one or more of the chain carbon atoms and the attached hydrogen atoms. The number or numbers proceding nor, dinor, etc., indicate which of the original prostanoic acid carbon atoms are missing in the named compound.

Each of the names of the PG analogs referred to herein contains (inter-p-phenylene), (inter-m-phenylene), or (inter-o-phenylene), preceded by two numbers. That indicates that p-phenylene, m-phenylene, or o-phenylene has been inserted between (inter) the two carbon atoms so numbered in the formula of prostanoic acid.

Thus, formula XII differs from $PGE_1$ and prostanoic acid in that an oxa oxygen replaces carbon 3, carbons 5 and 6 are missing, and m-phenylene is inserted between carbons 4 and 7.

Included in the above analogs are those with epi configuration for the hydroxy at C-15, illustrated by formula XIV. Where the C-15 configuration is the same as that of the natural prostaglandin $PGE_1$, identified as "S" configuration, the name ordinarily does not identify the configuration at C-15 unless there is 15-alkyl substitution. If the 15-epimer is intended, the name usually includes "15(R)" or "15-beta". See R. S. Cahn, Journal of Chemical Education 41, 116 (1964) for a discussion of S and R configurations. Formulas IV, VI, VIII, and X as printed represent optically active prostaglandin analogs with the same absolute configuration as $PGE_1$ or $PGF_{1\alpha}$ obtained from mammalian tissues. Formulas V, VII, IX, and XI represent their respective 15-epimers. Each of formulas IV–XI plus its mirror image describes a racemic mixture designated herein by the prefix "racemic" or "dl" before its name. When that prefix is absent, the intent is to designate an optically active compound represented by the appropriate formula.

In formulas IV-XI and wherever used in this disclosure, the term $C_nH_{2n}$ represents alkylene of one to 4 carbon atoms, inclusive; $C_pH_{2p}$ represents a valence bond or alkylene of one to 4 carbon atoms, inclusive, with one or 2 carbon atoms in the chain between the phenyl ring and —C—; $C_tH_{2t}$ represents a valence bond or alkylene of one to 10 carbon atoms, inclusive, substituted with zero, one, or 2 fluoro, and, when $C_tH_{2t}$ is alkylene, having one to 7 carbon atoms, inclusive, in the chain between —CR₃— and the phenyl ring; $R_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive; $R_2$ is alkyl of 2 to 10 carbon atoms, inclusive, substituted with zero, one, 2, or 3 fluoro; $R_3$ is hydrogen or alkyl of one to 4 carbon atoms, inclusive; T is alkyl of one to 4 carbon atoms, inclusive, fluoro, chloro, trifluoromethyl, or $OR_{17}$, wherein $R_{17}$ is hydrogen or alkyl of one to 4 carbon atoms, inclusive, and wherein s is zero, one, 2, or 3 with the proviso that not more than two T's are other than alkyl.

Each of the phenylene-oxa prostaglandin analogs represented by formula IV-XI is useful in place of the corresponding known prostaglandins for at least one of their known pharmacological purposes, which include reduction of gastric secretion, inhibition of blood platelet aggregation, increase of nasal patency, and labor inducement at term.

SUMMARY OF THE INVENTION

It is the purpose of this invention to provide intermediates useful in the preparation of phenylene-oxa prostaglandin analogs. It is a further purpose to provide novel processes for preparing these intermediates.

These intermediates include not only those which are useful for preparing the formula IV-XI analogs as disclosed in the above-identified German Offenlegungsschrift No. 2,209,990, but also phenylene-oxa prostaglandin analogs represented by the following formulas:

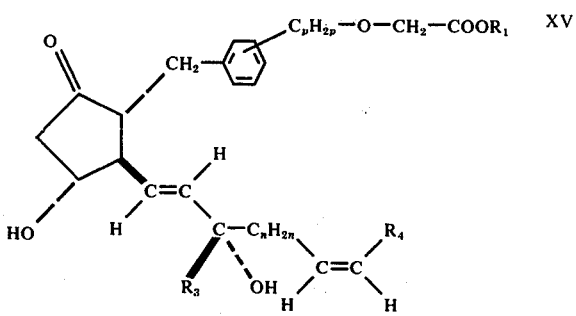

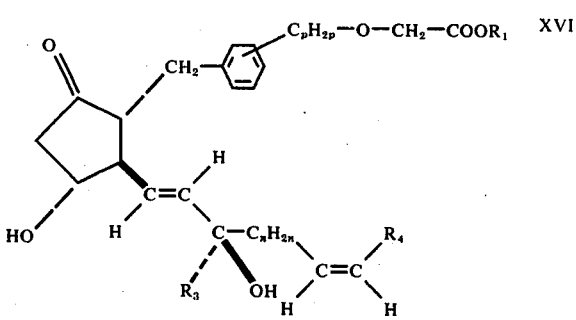

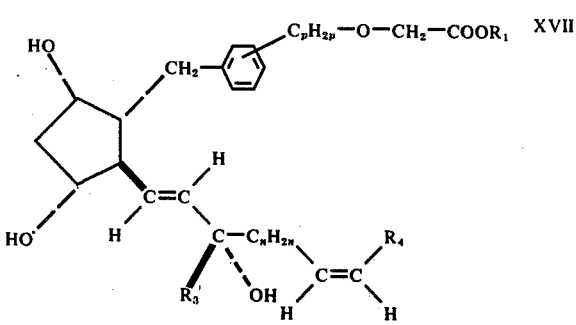

-continued

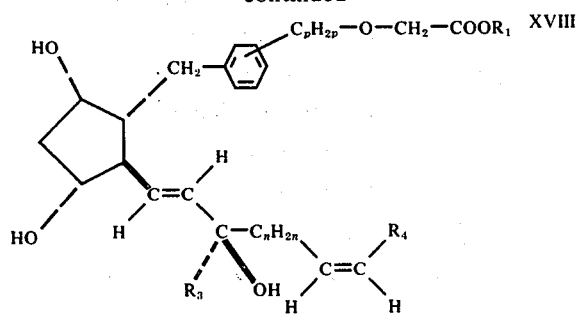 XVIII wherein $C_nH_{2n}$ represents alkylene of one to 4 carbon atoms, inclusive, and wherein $R_4$ is alkyl of one to 4 carbon atoms, inclusive, substituted with zero, one, 2, or 3 fluoro.

For example, a specific compound illustrating these analogs is represented by the following formula:

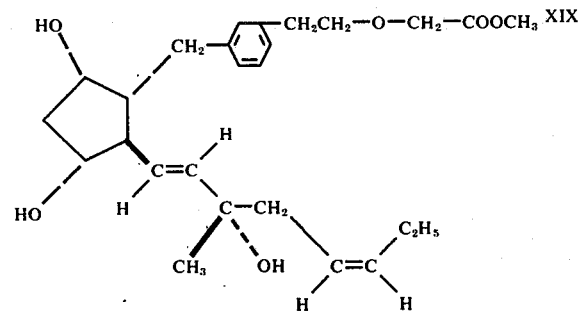 XIX

The compound of formula XIX is named 3-oxa-5,7-inter-m-phenylene-15(S)-15-methyl-17,18-didehydro-6-nor-PGF$_{1\alpha}$, methyl ester.

It is still a further purpose to provide intermediates useful in the preparation of novel phenylene prostaglandin analogs, including novel processes for preparing those intermediates.

As disclosed in a co-filed U.S. patent application by Norman A. Nelson, applicant's docket number 2528, those phenylene prostaglandin analogs are represented by the following formulas:

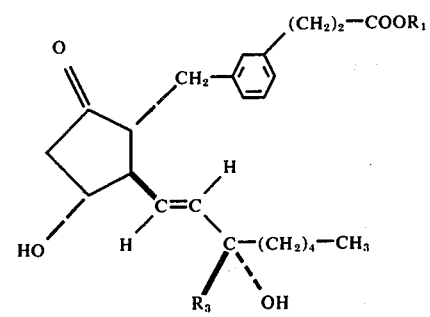 LVIII

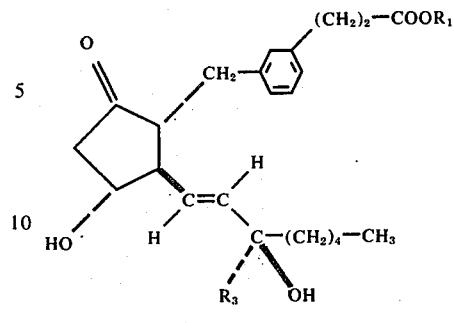 LIX

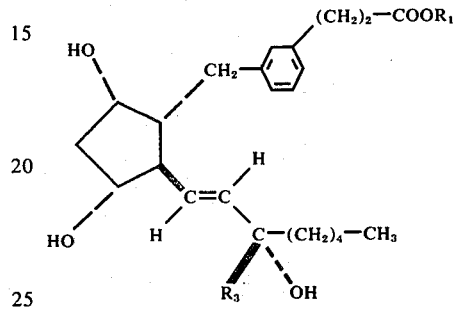 LX

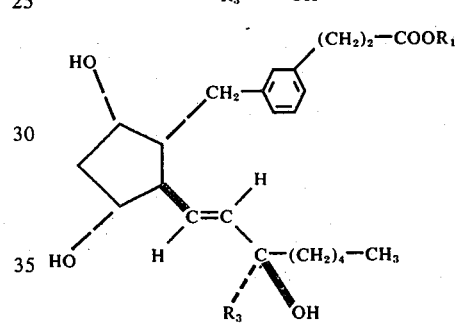 LXI wherein $R_1$ and $R_3$ have the same meaning as for the compounds above.

For convenience these phenylene compounds may be represented by the formulas

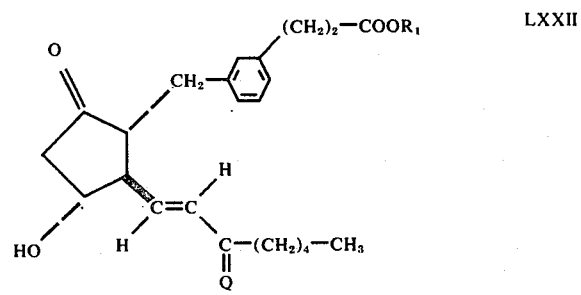 LXXII

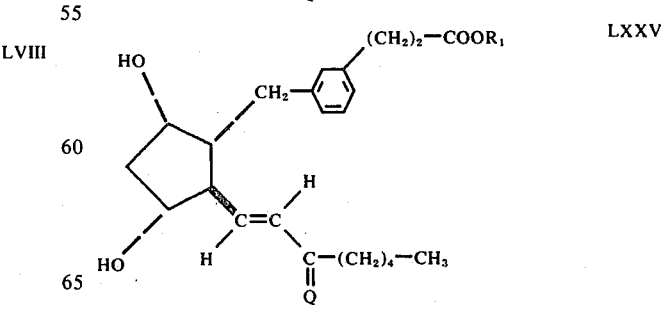 LXXV wherein Q is

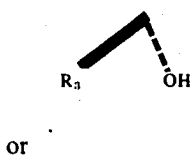

or

and $R_3$ and $R_1$ are as defined above.

For example, a specific compound illustrating these phenylene analogs is represented by the following formula

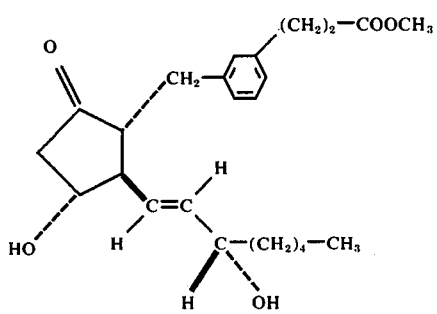

LXII

The compound of formula LXII is named 4,5,6-trinor-3,7-inter-m-phenylene-PGF$_1$, methyl ester.

Thus, for the phenylene-oxa compounds, there is provided an optically active compound of the formula

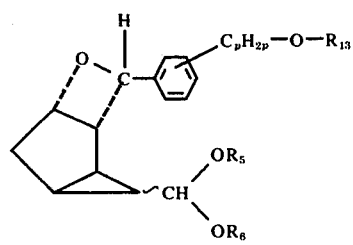

XX or a racemic mixture of that compound and the enantiomer thereof, wherein $C_pH_{2p}$ represents a valence bond or alkylene of one to 4 carbon atoms, inclusive, with one or 2 carbon atoms in the chain between the phenylene ring and —O—; wherein $R_5$ and $R_6$ are alkyl of one to 4 carbon atoms, inclusive, or, when taken together, the group represented by the formula

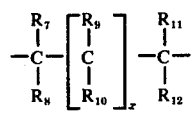

wherein $R_7$, $R_8$, $R_9$, $R_{10}$, $R_{11}$, and $R_{12}$ are hydrogen, alkyl of one to 4 carbon atoms, inclusive, or phenyl, with the proviso that not more than one of the R's is phenyl and the total number of carbon atoms is from 2 to 10, inclusive; and $x$ is zero or one; wherein $R_{13}$ is carboxyacyl of the formula $$R_{14}C-\overset{O}{\underset{\|}{}}$$

wherein $R_{14}$ is hydrogen, alkyl of one to 19 carbon atoms, inclusive, or aralkyl of 7 to 12 carbon atoms, inclusive, wherein alkyl or aralkyl are substituted with zero to 3 halo atoms; and wherein ~ indicates attachment to the cyclopropane ring in endo or exo configuration.

There is further provided an optically active compound of the formula

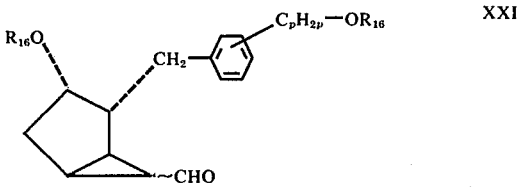

XXI or a racemic mixture of that compound and the enantiomer wherein $C_pH_{2p}$ is as defined above, ~ indicates attachment to the cyclopropane ring in exo or endo configuration, and $R_{16}$ is hydrogen or a blocking group, $R_{15}$, as defined below.

There is further provided an optically active compound of the formula

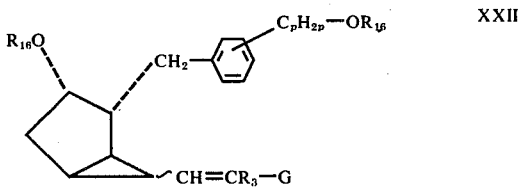

XXII or a racemic mixture of that compound and the enantiomer thereof, wherein $C_pH_{2p}$ and ~ are as defined above, wherein G is (1) $R_2$, which represents alkyl of 2 to 10 carbon atoms substituted with zero, one, 2, or 3 fluoro or (2) a monovalent moiety of the formula

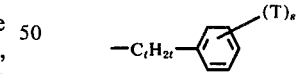

wherein $C_tH_{2t}$ represents a valence bond or alkylene of one to 10 carbon atoms, inclusive, substituted with zero, one, or 2 fluoro, said alkylene having one to 7 carbon atoms, inclusive, in the chain between —CR$_3$— and the phenyl ring, wherein T is alkyl of one to 4 carbon atoms, inclusive, fluoro, chloro, trifluoromethyl, or —OR$_{17}$, wherein R$_{17}$ is hydrogen or alkyl of one to 4 carbon atoms, inclusive, and wherein $s$ is zero, one, 2, or 3, with the proviso that not more than two T's are other than alkyl; wherein $R_{16}$ is hydrogen or a blocking group, $R_{15}$; and wherein $R_3$ is hydrogen or alkyl of one to 4 carbon atoms, inclusive.

There is further provided an optically active compound of the formula

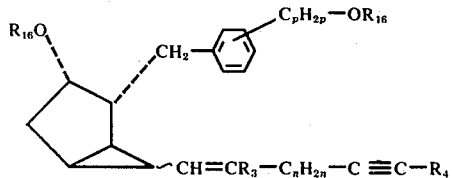 XXIII

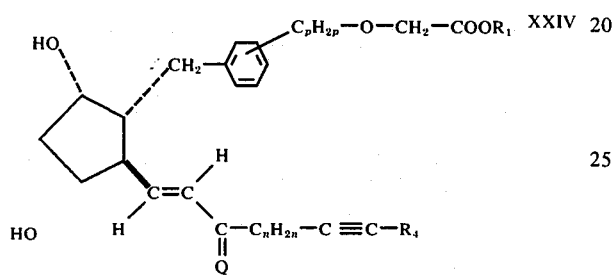

or a racemic mixture of that compound and the enantiomer thereof, wherein $C_pH_{2p}$, $R_3$, $R_{16}$, and ~ are as defined above; wherein $C_nH_{2n}$ is alkylene of one to 4 carbon atoms, inclusive; and wherein $R_4$ is alkyl of one to 4 carbon atoms, inclusive, substituted with zero, one, 2, or 3 fluoro.

There is further provided an optically active compound of the formula

or

wherein $R_3$ is as defined above; and wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive.

There is likewise provided a process for preparing an optically active compound of the formula

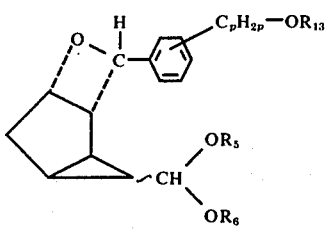 XX or a racemic mixture of that compound and the enantiomer thereof, wherein $C_pH_{2p}$ represents a valence bond or alkylene of one to 4 carbon atoms, inclusive, with one or 2 carbon atoms in the chain between the phenylene ring and —O—; wherein $R_5$ and $R_6$ are alkyl of one to 4 carbon atoms, inclusive, or, when taken together,

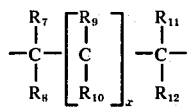

wherein $R_7$, $R_8$, $R_9$, $R_{10}$, $R_{11}$, and $R_{12}$ are hydrogen, alkyl of one to 4 carbon atoms, inclusive, or phenyl, with the proviso that not more than one of the R's is phenyl and the total number of carbon atoms is from 2 to 10, inclusive; and $x$ is zero or one; wherein $R_{13}$ is carboxyacyl of the formula

wherein $R_{14}$ is hydrogen, alkyl of one to 19 carbon atoms, inclusive, or aralkyl of 7 to 12 carbon atoms, inclusive, wherein alkyl or aralkyl are substituted with zero to 3 halo atoms; and wherein ~ indicates attachment to the cyclopropane ring in endo or exo configuration, which comprises reacting an optically active compound of the formula

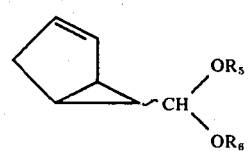 XXX or a racemic mixture of that compound and the enantiomer thereof, wherein ~, $R_5$ and $R_6$ are as defined above, with a compound of the formula

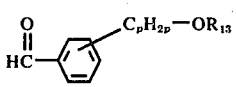 XXVI wherein $C_pH_{2p}$ and $R_{13}$ are as defined above.

There is further provided a process for preparing an optically active compound of the formula

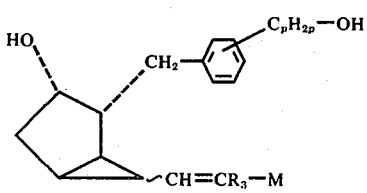 XXVII or a racemic mixture of that compound and the enantiomer thereof, wherein $C_pH_{2p}$ represents a valence bond or alkylene of one to 4 carbon atoms, inclusive, with one or 2 carbon atoms in the chain between the phenylene ring and —O—; wherein M is a hydrocarbyl or substituted hydrocarbyl group, being (1) $R_2$, wherein $R_2$ is alkyl of 2 to 10 atoms substituted with zero, one, 2, or 3 fluoro; (2) a monovalent moiety of the formula

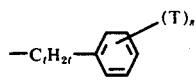

wherein $C_tH_{2t}$ represents a valence bond or alkylene of one to 10 carbon atoms, inclusive, substituted with zero, one, or 2 fluoro, and, when $C_tH_{2t}$ is alkylene, having one to 7 carbon atoms, inclusive, in the chain between —$CR_3$— and the phenyl ring, wherein T is alkyl of one to 4 carbon atoms, inclusive, fluoro, chloro, trifluoromethyl, or —$OR_{17}$, wherein $R_{17}$ is hydrogen or alkyl of one to 4 carbon atoms, inclusive, and wherein s is zero, one, 2, or 3 with the proviso that not more than two T's are other than alkyl; or (3) a group represented by the formula

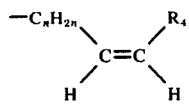

wherein $C_nH_{2n}$ is alkylene of one to 4 carbon atoms, inclusive, and $R_4$ is alkyl of one to 4 carbon atoms, inclusive, substituted with zero, one, 2, or 3 fluoro; and wherein ~ indicates attachment to the cyclopropane ring in alpha or beta configuration; which comprises treating an optically active compound of the formula

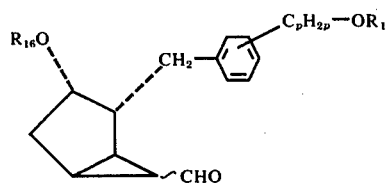

XXVIII or a racemic mixture of that compound and the enantiomer thereof wherein $R_{16}$ is hydrogen or a blocking group $R_{15}$, and wherein $C_pH_{2p}$ and ~ are as defined above, with a Wittig reagent prepared from a compound of the formula

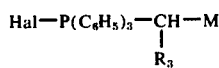

XXIX wherein Hal is chloro, bromo, or iodo, and M and $R_3$ are as defined above; with the proviso that when $R_{16}$ in the product is hydrogen, $R_{15}$ is replaced with hydrogen.

Likewise, for the phenylene compounds, there if provided an optically active compound of the formula

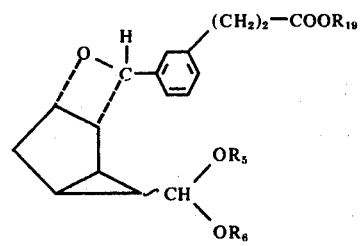

LXIII or a racemic mixture of that compound and the enantiomer thereof, $R_{19}$ is hydrogen or alkyl of one to 4 carbon atoms, inclusive; wherein $R_5$, $R_6$, and ~ are as defined above.

There is further provided an optically active compound of the formula

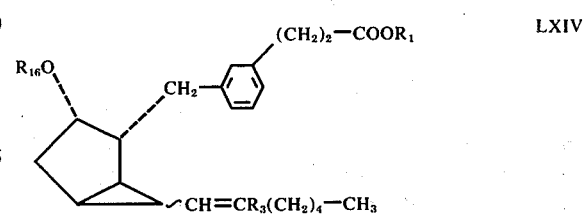

LXIV or a racemic mixture of that compound and the enantiomer thereof, wherein $R_1$, $R_3$m and ~ are as defined above, and wherein $R_{16}$ is hydrogen or a blocking group $R_{15}$ as defined herein.

There is further provided a process for preparing an optically active compound of the formula

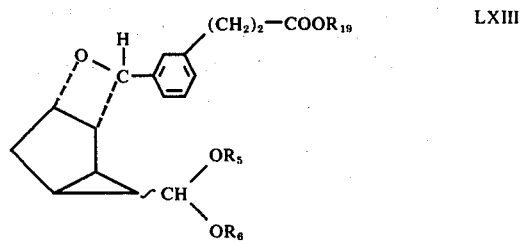

LXIII or a racemic mixture of that compound and the enantiomer thereof, wherein $R_5$, $R_6$, $R_{19}$, and ~ are as defined above, by reacting an optically active compound of the formula

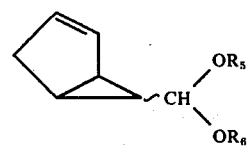

XXX or a racemic mixture of that compound and the enantiomer thereof, wherein $R_5$, $R_6$, and ~ are as defined above, with a compound of the formula

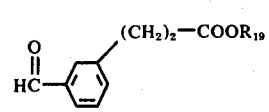

wherein $R_{19}$ is as defined above.

There is further provided a process for preparing an optically active compound of the formula

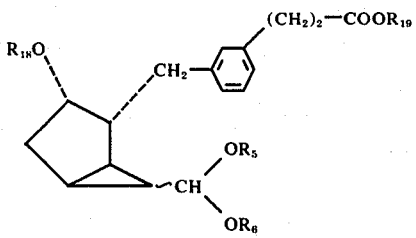 LXV

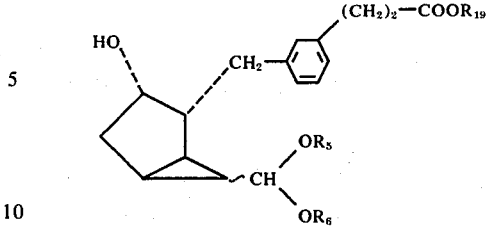 LXVI or a racemic mixture of that compound and the enantiomer thereof, wherein $R_5$, $R_6$, $R_{19}$, and ~ are as defined above and wherein $R_{18}$ represents hydrogen, carboxyacyl $R_{13}$ as defined above; benzoyl and substituted benzoyl as represented by

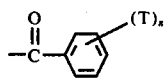

wherein T is alkyl of one to 4 carbon atoms, inclusive, phenylalkyl of 7 to 10 carbon atoms, inclusive, or nitro, and s is zero to 5, inclusive, provided that not more than two T's are other than alkyl, and that the total number of carbon atoms in the T's does not exceed 10 carbon atoms; mono-esterified phthaloyl as represented by

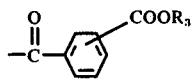

wherein $R_3$ is alkyl of one to 4 carbon atoms, inclusive; or naphthoyl and substituted naphthoyl as represented by

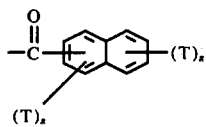

wherein T and s are as defined above; by (1) hydrogenating an optically active compound of the formula

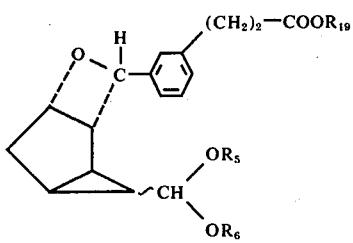 LXIII or a racemic mixture of that compound and the enantiomer thereof, wherein $R_5$, $R_6$, $R_{19}$, and ~ are as defined above, in the presence of a noble metal catalyst so as to obtain a compound of the formula or a racemic mixture of that compound and the enantiomer thereof, wherein $R_5$, $R_6$, $R_{19}$, and ~ are as defined above, and (2) reacting the product of step (1) with an acylating agent.

The above novel intermediates of formulas XX–XXV and LXIII–LXVI are transformed into the products of formulas IV–XVIII and LVIII–LXI by processes described below.

With regard to formulas IV to XVIII and XX to XXV, examples of alkyl of one to 4 carbon atoms, inclusive, are methyl, ethyl, propyl, butyl, and isomeric forms thereof. Examples of alkyl of one to 12 carbon atoms, inclusive, are those given above, and pentyl, hexyl, heptyl, octyl, nonyl, decyl, undecyl, dodecyl, and isomeric forms thereof. Examples of alkyl of one to 19 carbon atoms, inclusive, are those given above, and tridecyl, tetradecyl, pentadecyl, hexadecyl, octadecyl, nonadecyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 3-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralykyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-napthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of alkyl of one to 10 carbon atoms, inclusive, substituted with one to 3 fluoro, are trifluoromethyl, 2-fluoroethyl, 2-fluorobutyl, 3-fluorobutyl, 4-fluorobutyl, 5-fluoropentyl, 4-fluoro-4-methylpentyl, 3-fluoroisoheptyl, 8-fluorooctyl, 3,4-difluorobutyl, 4,4-difluoropentyl, 5,5-difluoropentyl, 5,5,5-trifluoropentyl, and 10,10,10-trifluorodecyl.

Examples of alkylene within the various scopes of $C_pH_{2p}$, $C_nH_{2n}$, and $C_tH_{2t}$, as those are defined above, are methylene, ethylene, trimethylene, tetramethylene, pentamethylene, hexamethylene, and heptamethylene, and those alkylene with one or more alkyl substituents on one or more carbon atoms thereof, e.g., —CH(CH$_3$)—, —C(CH$_3$)$_2$—.

Examples of alkylene of one to 4 carbon atoms, inclusive, with one or 2 carbon atoms in the chain are methylene, ethylene, —CH(CH$_3$)—, —C(CH$_3$)$_2$—, —CH(CH$_2$CH$_3$)—, —CH$_2$—CH(CH$_3$)—, —CH(CH- $_3$)—CH(CH$_3$)—, and —CH$_2$—C(CH$_3$)$_2$—. Examples of alkylene of one to 4 carbon atoms, inclusive, include those given above, and trimethylene and tetramethylene. Examples of alkylene of one to 9 carbon atoms, inclusive, with one to 5 carbon atoms, inclusive, in the chain include those given above, pentamethylene, and —CH(CH$_3$)—CH$_2$—, —C(CH$_3$)$_2$—CH$_2$—, —CH$_2$—CH(CH$_3$)—CH$_2$—, —CH$_2$—CH$_2$—CH(CH$_2$CH$_3$)—, —CH$_2$—CH$_2$—CH(CH$_2$CH$_2$CH$_3$)—, —CH(CH$_3$)—CH(CH$_3$)—CH$_2$—CH$_2$—, —CH$_2$—CH$_2$—CH$_2$—C(CH$_3$)$_2$—CH$_2$—, —(CH$_2$)$_4$—CH(CH$_3$)—, and —C(CH$_3$)$_2$—CH$_2$—CH$_2$—CH$_2$—C(CH$_3$)$_2$—. Examples of alkylene of one to 10 carbon atoms, inclusive, substituted with zero, one, or 2 fluoro, and having one to 7 carbon atoms, inclusive, in the chain, include those given above, hexamethylene, heptamethylene, and —C(CH$_3$)$_2$—(CH$_2$)$_3$—, —C(CH$_3$)$_2$—(CH$_2$)$_4$—, —C(CH$_3$)$_2$—(CH$_2$)$_5$—, —C(CH$_3$)$_2$—(CH$_2$)$_6$—, —CHF—CH$_2$—, —CHF —CHF—, —CF$_2$—CH$_2$—, —CF$_2$—CH$_2$—CH$_2$—, —CF$_2$—CH$_2$—CF$_2$—, —CH$_2$—CHF—CH$_2$, —CH$_2$—CH$_2$—CF (CH$_3$)—, —(CH$_2$)$_3$—CF$_2$—, —CF$_2$—(CH$_2$)$_3$—, —CF$_2$—(CH$_2$)$_6$—and —CHF—(CH$_2$)$_6$—.

Examples of

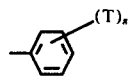

as defined above are phenyl, p-tolyl, m-tolyl, o-tolyl, p-fluorophenyl, m-fluorophenyl, o-fluorophenyl, p-chlorophenyl, m-chlorophenyl, o-chlorophenyl, p-trifluoromethylphenyl, m-trifluoromethylphenyl, o-trifluoromethylphenyl, p-hydroxyphenyl, o-methoxyphenyl, m-methoxyphenyl, p-methoxyphenyl, o-ethoxyphenyl, m-isopropoxyphenyl, o-ethylphenyl, m-isopropylphenyl, p-tert-butylphenyl, p-butoxyphenyl, 3,4-dimethylphenyl, 2,4-diethylphenyl, 2,4,6-trimethylphenyl, 3,4,5-trimethylphenyl, 2,4-dichlorophenyl, 3,4-difluorophenyl, 2-chloro-4-methylphenyl, 2-fluoro-4-methoxyphenyl, 3,5-dimethyl-4-fluorophenyl, 2,6-dimethyl-4-hydroxyphenyl, and 2,4-di(trifluoromethyl)phenyl.

The novel intermediates of this invention, including the formula XX—XXVIII compounds above, are useful for preparing the analogs of formula IV-XI above. The pharmacological utility of the end-products is disclosed in the above-identified German Offenlegungsschrift No. 2,209,990. Certain ones of these intermediates are also useful in preparing the analogs of formula XV-XVIII. Those analogs are not the subject of this invention, but each of them is useful in place of the corresponding known prostaglandins for at least one of their known pharmacological purposes.

In accordance with the preferences disclosed in the above-identified German Offenlegunsschrift for certain compounds within the scope of formulas IV-XI, certain of the novel intermediates of this invention are preferred. For example, in the compounds of formulas XX, XXI, and XXII, C$_p$H$_{2p}$ is preferably a valence bond or methylene; likewise, ~ is preferably endo. In the compounds of formula XXII wherein G is R$_2$, it is preferred that R$_2$ be

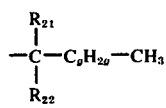

wherein C$_g$H$_{2g}$ is alkylene of one to 9 carbon atoms, inclusive, with one to 5 carbon atoms, inclusive, in the chain between —CR$_{21}$R$_{22}$— and terminal methyl, wherein R$_{21}$ and R$_{22}$ are hydrogen, alkyl of one to 4 carbon atoms, inclusive, or fluoro, being the same or different with the proviso that R$_{22}$ is fluoro only when R$_{21}$ is hydrogen or fluoro. Especially preferred are those formula-XXII compounds wherein R$_2$ is —CHF—(CH$_2$)$_3$—CH$_3$, —CF$_2$—(CH$_2$)$_3$—CH$_3$, —CH(CH$_3$)—(CH$_2$)$_3$CH$_3$, —C(CH$_3$)$_2$—(CH$_2$)$_3$—CH$_3$, or —C(C$_2$H$_5$)$_2$—(CH$_2$)$_3$—CH$_3$. In the compounds of formula XXII wherein G is

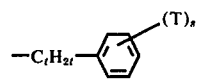

it is preferred that C$_t$H$_{2t}$ be a valence bond or alkylene of one to 4 carbon atoms, inclusive, i.e. —(CH$_2$)$_d$— wherein d is one, 2, 3, or 4, with or without fluoro or alkyl substituted carbon (C-15), e.g. —CHF—(CH$_2$)$_e$—, —CF$_2$—(CH$_2$)$_e$—, —CH(CH$_3$)—(CH$_2$)$_e$—, or —C(CH$_3$)$_2$—(CH$_2$)$_e$—, wherein e is zero, one, 2, or 3. In the compounds of formula XXII, R$_3$ is preferably hydrogen or methyl.

In compounds of formulas XXIII and XXIV it is preferred that C$_p$H$_{2p}$ be a valence bond or methylene, that C$_n$H$_{2n}$ be methylene and that R$_4$ be ethyl to yield preferred compounds of formulas XV-XVIII.

Reference to Chart A will make clear the steps by which starting material XXX is transformed to product XXXVI. The formula-XXX compound wherein R$_5$ and R$_6$ together are —CH$_2$—C(CH$_3$)$_2$—CH$_2$— and ~ is endo, i.e. bicyclo [3.1.0]hex-2-ene-6-endo-carboxaldehyde neopentyl glycol acetal, is available either in racemic or optically active form. See U.S. Pat. No. 3,711,515 for both the endo and exo forms.

In Chart A the symbols used therein have the same meanings as defined above, as to C$_p$H$_{2p}$, G, $_1$, R$_1$, R$_3$, R$_5$, R$_6$, R$_{13}$, R$_{16}$, R$_{18}$, and ~.

CHART A

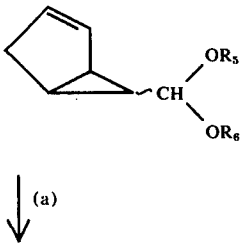

XXX (a)

CHART A-continued
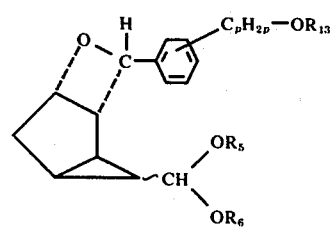   XX
↓ (b)
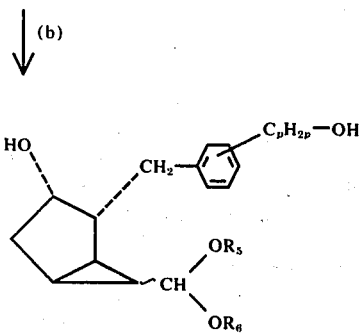   XXXI
↓ (c)
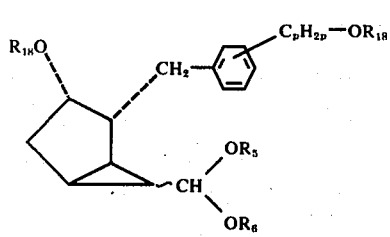   XXXII
↓ (d)
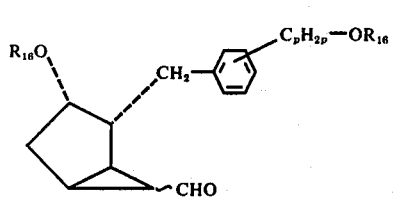   XXI
↓ (e)
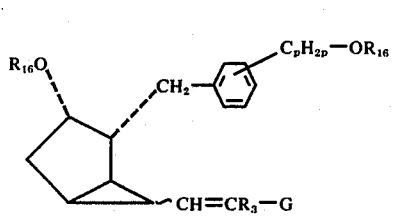   XXII
↓ (f)

CHART A-continued

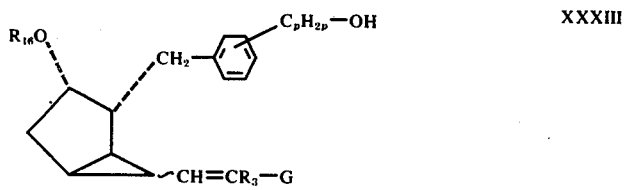

XXXIII

↓ (g)

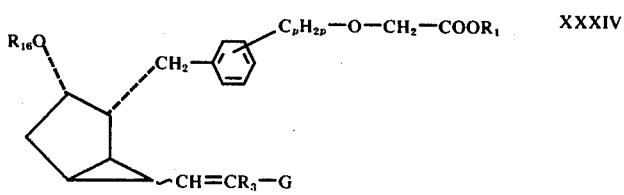

XXXIV

↓ (h)

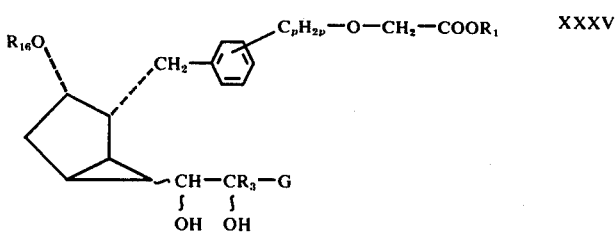

XXXV

↓ via several steps

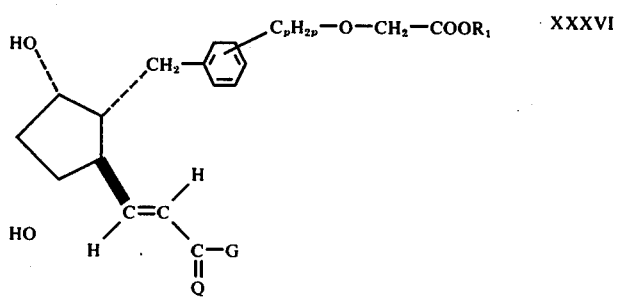

XXXVI

Furthermore, in Chart A and likewise in the other charts of this specification, the formulas as drawn represent specific optical isomers following the conventions applied herein to the end products. However, for purposes of convenience and brevity it is intended that such representations of the process steps for the optically active intermediates are applicable to those same process steps as used for the corresponding racemic intermediates.

Both the endo and exo forms of bicyclo hexene XXX are available or are made by methods known in the art, in either their racemic or optically active forms. See U.S. Pat. No. 3,711,515. Either the endo or exo starting material will yield the ultimate analogs of formula XXXVI by the process of Chart A.

In step (a) oxetane XX is obtained by reaction of the formula-XXX bicyclo hexene with an aldehyde of the formula

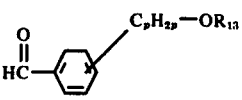

XXVI wherein $C_pH_{2p}$ represents a valence bond or alkylene of one to 4 carbon atoms, inclusive, with one or 2 carbon atoms in the chain between the phenyl ring and —O—, and wherein $R_{13}$ is carboxyacyl of the formula

wherein $R_{14}$ is hydrogen alkyl of one to 19 carbon atoms, inclusive, or aralkyl of 7 to 12 carbon atoms, inclusive, wherein alkyl or aralkyl are substituted with zero to 3 halo atoms.

The formula-XXVI aldehydes are available or readily prepared by methods known in the art. Examples of such compounds within the scope of formula XXVI are:

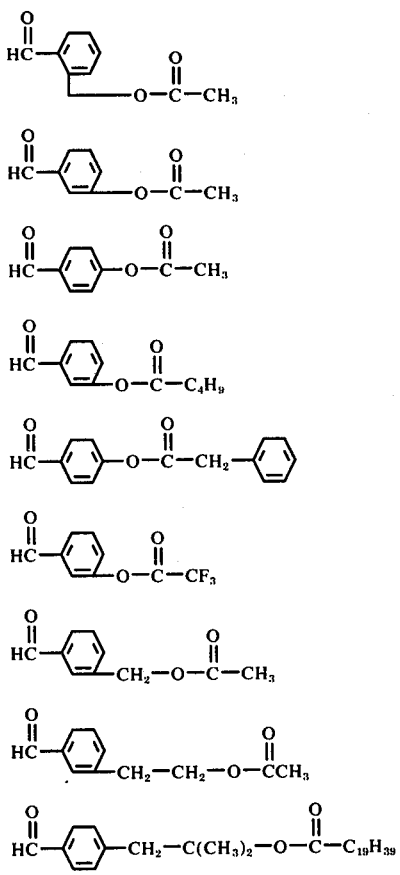

The formation of oxetane XX is accomplished by photolysis of a mixture of the bicyclo hexene and the aldehyde in a solvent. The bicyclo hexene is preferably used in excess over the molar equivalent, for example 2 to 4 times the theoretical equivalent amount. The solvent is a photochemically inert organic liquid, for example liquid hydrocarbons, including benzene or hexane, 1,4-dioxane, and diethyl ether. The reaction is conveniently done at ambient conditions, for example 25° C., but may be done over a wide range of temperature, from about −78° C. to the boiling point of the solvent. The irradiation is done with mercury vapor lamps of the low or medium pressure type, for example those peaking at 3500 A. Such sources are available from The Southern New England Ultraviolet Co., Middletown, Conn. Alternatively, those lamps which emit a broad spectrum of wavelengths and which may be filtered to transmit only light of λ∼3000–3700 A may also be used. For a review of photolysis see D. R. Arnold in "Advances in Photochemistry", Vol. 6, W. A. Noyes et al., Wiley-Interscience, New York, 1968, pp. 301–423.

In step (b) the cleavage of the oxetane ring to yield the formula-XXXI compounds is accomplished with an alkali metal in the presence of a primary amine or alcohol. Preferred is lithium in ethylamine, or sodium in ethyl alcohol. See L. J. Altman et al., Synthesis 129 (1974). The cleavage transformation may also be accomplished by catalytic hydrogenation over an inert metal catalyst, e.g. Pd on carbon, in ethyl acetate or ethanol.

In step (c) the formula XXXI diol is prepared for step (d) by preferably blocking the two hydroxyl groups with carboxyacyl groups within the scope of $R_{13}$ as defined above, i.e. $R_{14}C(O)$—wherein $R_{14}$ is hydrogen, alkyl of one to 19 carbon atoms, inclusive, or aralkyl of 7 to 12 carbon atoms, inclusive, wherein alkyl or aralkyl are substituted with zero to 3 halo atoms. For example, the diol is treated with an acid anhydride such as acetic anhydride, or with an acyl halide in a tertiary amine. Especially preferred is pivaloyl chloride in pyridine.

Other carboxyacylating agents useful for this transformation are known in the art or readily obtainable by methods known in the art, and include carboxyacyl halides, preferably chlorides, bromides, or fluorides, i.e. $R_{14}C(O)Cl$, $R_{14}C(O)Br$, or $R_{14}C(O)F$, and carboxyacid anhydrides,

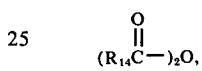

wherein $R_{14}$ is as defined above. The preferred reagent is an acid anhydride. Examples of acid anhydrides useful for this purpose are acetic anhydride, propionic anhydride, butyric anhydride, pentanoic anhydride, nonanoic anhydride, tridecanoic anhydride, stearic anhydride, (mono, di, or tri) chloroacetic anhydride, 3-chlorovaleric anhydride, 3-(2-bromoethyl)-4,8-dimethylnonanoic anhydride, cyclopropaneacetic anhydride, 3-cycloheptanepropionic anhydride, 13-cyclopentanetridecanoic anhydride, phenylacetic anhydride, (2 or 3)-phenylpropionic anhydride, 13-phenyltridecanoic anhydride, and phenoxyacetic anhydride. The choice of anhydride depends upon the identity of $R_{14}$ in the final acylated product, for example when $R_{14}$ is to be methyl, acetic anhydride is used; when $R_{14}$ is to be 2-chlorobutyl, 3-chlorovaleric anhydride is used.

When $R_{14}$ is hydrogen,

is formyl. Formylation is carried out by procedures known in the art, for example, by reaction of the hydroxy compound with the mixed anhydride of acetic and formic acids or with formylimidazole. See, for example, Fieser et al., Reagents for Organic Synthesis, John Wiley and Sons, Inc., pp. 4 and 407 (1967) and references cited therein. Alternatively, the formula XXXI diol is reacted with two equivalents of sodium hydride and then with excess ethyl formate.

In formula XXXII, $R_{18}$ may also represent a blocking group such as benzoyl, substituted benzoyl, monoesterified phthaloyl, naphthoyl and substituted naphthoyl. For introducing those blocking groups, methods known in the art are used. Thus, an aromatic acid of the formula $R_{18}OH$, wherein $R_{18}$ is as defined above, for example benzoic acid, is reacted with the formula-XXXI compound in the presence of a dehydrating agent, e.g. sulfuric acid, zinc chloride, or phosphoryl chloride; or an anhydride of the aromatic acid of the formula $(R_{18})_2O$, for example benzoic anhydride, is used.

As examples of reagents providing $R_{18}$ for the purposes of this invention, the following are available as acids ($R_{18}OH$), anhydrides (($R_{18})_2O$), or acyl chlorides ($R_{18}Cl$): benzoyl; substituted benzoyl, e.g, (2-, 3-, or 4-)methylbenzoyl, (2-, 3-, or 4-)ethylbenzoyl, (2-, 3-, or 4-)isopropylbenzoyl), (2-, 3-, or 4-)tert-butylbenzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-, 3-, or 4-(toluyl, 2-, 3-, or 4-) 4-phenethylbenzoyl, 2-, 3-, or 4-nitrobenzoyl, (2,4-, 2,5-, or 3,5-)dinitrobenzoyl, 4,5-dimethyl-2-nitrobenzoyl, 2-nitro-6-phenethylbenzoyl, 3-nitro-2-phenethylbenzoyl; mono-esterified phthaloyl, e.g.

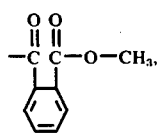

isophthaloyl, e.g.

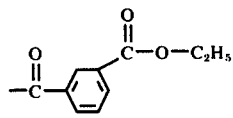

or terephthaloyl, e.g.,

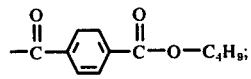

(1- or 2-)naphthoyl; and substituted naphthoyl, e.g. (2-, 3-, 4-, 5-, 6-, or 7-)-methyl-1-naphthoyl, (2-or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, 8-benzyl-1-naphthoyl, (3-, 4-, 5-, or 8-)-nitro-1-naphthoyl, 4,5-dinitro-1-naphthoyl, (3-, 4-, 6-, 7- or 8-)-methyl-1-naphthoyl, 4-ethyl-2-naphthoyl, and (5- or 8-)-nitro-2-naphthoyl.

Examples of aromatic acid anhydrides useful for this purpose are benzoic anhydride, (o, m, or p)-bromobenzoic anhydride, 2,4(or 3,4)-dichlorobenzoic anhydride, p-trifluoromethylbenzoic anhydride, 2-chloro-3-nitrobenzoic anhydride, (o, m, or p)-nitrobenzoic anhydride, (o, m, or p)-toluic anhydride, 4-methyl-3-nitrobenzoic anhydride, 4-octylbenzoic anhydride, (2,3, or 4)-biphenylcarboxylic anhydride, 3-chloro-4-biphenylcarboxylic anhydride, 5-isopropyl-6-nitro-3-biphenylcarboxylic anhydride, and (1 or 2)-naphthoic anhydride.

Preferably, however, an acyl halide, e.g. $R_{18}Cl$, for example benzoyl chloride, is reacted with the formula-XXXI compound in the presence of a tertiary amine such as pyridine, triethylamine, and the like. The reaction is carried out under a variety of conditions using procedures generally known in the art. Generally, mild conditions are employed, e.g. 20°–60° C., contacting the reactants in a liquid medium, e.g. excess pyridine or an inert solvent such as benzene, toluene or chloroform. The acylating agent is used either in stoichiometric amount or in excess. There may be employed, therefore, benzoyl chloride, 4-nitrobenzoyl chloride, 3,5-dinitrobenzoyl chloride, and the like, i.e. $R_{18}Cl$ compounds corresponding to the above $R_{18}$ groups. If the acyl chloride is not available, it is made from the corresponding acid and phosphorus pentachloride as is known in the art.

In step (d), the formula-XXXII acetal is converted to aldehyde XXI by acid hydrolysis, known in the art, using dilute mineral acids, acetic or formic acids, and the like. Solvents such as acetone, dioxane, and tetrahydrofuran are used.

For steps (e) through (h) it is optional whether $R_{16}$ be hydrogen or a "blocking group" as defined below. For efficient utilization of the Wittig reagent it is preferred that $R_{16}$ be a blocking group. If the formula-XXXII compound is used wherein $R_{18}$ is hydrogen, the formula-XXI intermediate will have hydrogen at $R_{16}$. If $R_{16}$ is to be a blocking group, that may be readily provided prior to step (e) by reaction with suitable reagents as discussed below.

The blocking group, $R_{15}$, is any group which replaces hydrogen of the hydroxyl groups, which is not attacked by nor is reactive to the reagents used in the respective transformations to the extent that the hydroxyl group is, and which is subsequently replaceable by hydrogen at a later stage in the preparation of the prostaglandin-like products.

Several blocking groups are known in the art, e.g. tetrahydropyranyl, acetyl, and p-phenylbenzoyl (see Corey et al., J. Am. Chem. Soc. 93, 1491 (1971)).

Those which have been found useful include (a) carboxyacyl within the scope of $R_{13}$ above, i.e. acetyl, and also benzoyl, naphthoyl, and the like; (b) tetrahydropyranyl; (c) tetrahydrofuranyl; (d) a group of the formula

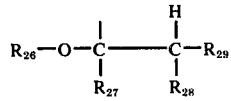

wherein $R_{26}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{27}$ and $R_{28}$ are the same or different, being hydrogen, alkyl of one to 4 carbon atoms, inclusive, phenyl or phenyl substituted with one, 2, or 3 alkyl of one to 4 carbon atoms, inclusive, or, when $R_{27}$ and $R_{28}$ are taken together, —(CH$_2)_a$— or —(CH$_2)_b$—O—(CH$_2)_c$— wherein $a$ is 3, 4, or 5, $b$ is one, 2, or 3, and $c$ is one, 2, or 3 with the proviso that b plus c is 2, 3, or 4, and wherein $R_{29}$ is hydrogen or phenyl; or (e) —Si(A)$_3$ wherein A is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive.

In replacing the hydrogen atoms of the hydroxyl groups with carboxyacyl, benzoyl, naphthoyl, etc. blocking groups, methods known in the art are used. The reagents and conditions are discussed above for $R_{18}$ on compound XXXII.

When the blocking group is tetrahydropyranyl or tetrahydrofuranyl, the appropriate reagent, e.g. 2,3-dihydropyran or 2,3-dihydrofuran, is used in an inert solvent such as dichloromethane, in the presence of an acid condensing agent such as p-toluenesulfonic acid or pyridine hydrochloride. The reagent is used in slight excess, preferably 1.0 to 1.2 times theory. The reaction is carried out at about 20°–50° C.

When the blocking group is of the formula

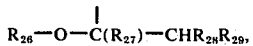

as defined above, the appropriate reagent is a vinyl ether, e.g. isobutyl vinyl ether or any vinyl ester of the formula $R_{26}-O-C(R_{27})=CR_{28}R_{29}$ wherein $R_{26}$, $R_{27}$, $R_{28}$, and $R_{29}$ are as defined above; or an unsaturated cyclic or heterocyclic compound, e.g. 1-cyclohex-1-yl methyl ether

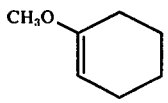

or 5,6-dihydro-4-methoxy-2H-pyran

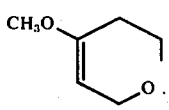

see C. B. Reese et al., J. Am. Chem. Soc. 89, 3366 (1967). The reaction conditions for such vinyl ethers and unsaturates are similar to those for dihydropyran above.

When the blocking group is silyl of the formula —Si-(A)$_3$, the formula-XXI compound is transformed to a silyl derivative of formula XXI by procedures known in the art. See, for example, Pierce, "Silylation of Organic Compounds," Pierce Chemical Co., Rockford, Illinois (1968). The necessary silylating agents for these transformations are known in the art or are prepared by methods known in the art. See, for example, Post "Silicones and Other Organic Silicon Compounds," Reinhold Publishing Corp., New York, N.Y. (1949). These reagents are used in the presence of a tertiary base such as pyridine at temperatures in the range of about 0° to +50° C. Examples of trisubstituted mono-chlorosilanes suitable for this purpose include chlorotrimethylsilane, chlorotriisobutylsilane, chlorotriphenylsilane, chlorotris(p-chlorophenyl)silane, chlorotri-m-tolylsilane, and tribenzylchlorosilane. Alternately, a chlorosilane is used with a corresponding disilazane. Examples of other silylating agents suitable for forming the formula-XXI interemdiates include pentamethylsilylamine, pentaethylsilylamine, N-trimethylsilydiethylamine, 1,1,1-triethyl-N,N-dimethylsilylamine, N,N-diisopropyl-1,1,1-trimethylsilylamine, 1,1,1-tributyl-N,N-dimethylsilylamine N,N-dibutyl-1,1,1-trimethylsilylamine, 1-isobutyl-N,N,1,1-tetramethylsilylamine, N-benzyl-N-ethyl-1,1,1-trimethylsilylamine, N,N,1,1-tetramethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilylamine, and 1-methyl-N,N,1,1-tetraphenylsilylamine.

In step (e) the aldehyde group is transformed by the Wittig reaction to a moiety of the formula —CH=CR$_3$G. For this purpose a phosphonium salt prepared from an organic chloride or bromide of the formula

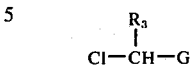

or

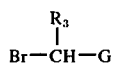

is employed, wherein G and $R_3$ are as defined above. These organic chlorides or bromides are known in the art or are readily prepared by methods known in the art. See for example the above-identified German Offenlegungsschrift No. 2,209,990. As to the Wittig reaction, see, for example, U.S. Pat. No. 3,776,941 and references cited therein.

In step (f) compound XXXIII is obtained by deblocking if necessary. When $C_pH_{2p}$ is a valence bond, and $R_{16}$ is a hindered carboxyacyl,

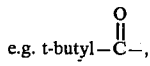

$R_{15}$ on the phenolic hydroxy is selectively replaced with hydrogen by hydrolysis with sodium or potassium hyroxide in ethanol-water. Instead of ethanol, other water-miscible solvents may be substituted, for example 1,4-dioxane, tetrahydrofuran, or 1,2-dimethoxyethane. The selective hydrolysis is preferably carried out at −15° to 25° C. Higher temperatures may be used but with some decrease in selectivity.

Total hydrolysis of $R_{16}$ blocking groups on compound XXII is accomplished, when $R_{16}$ is carboxyacyl, with an alkali alkoxide in an alcoholic solvent, preferably sodium methoxide in methanol at a temperature from 25° C. to reflux. When $R_{16}$ is tetrahydropyranyl, aqueous acid, e.g. dilute acetic acid, is used at 25° to 50° C. When $R_{16}$ is trialkylsilyl, either aqueous acid or base are used at 25° to 50° C.

Continuing with Chart A, in step (g) a Williamson synthesis is employed to obtain compound XXXIV. The formula-XXXIII alcohol or phenol is condensed with a haloacetate within the scope of Hal—CH$_2$—COOR$_1$ wherein Hal is chloro, bromo, or iodo and $R_1$ is as defined above. Normally the reaction is done in the presence of a base such as n-butyllithium, phenyllithium, triphenylmethyllithium, sodium hydride, potassium t-butoxide sodium hydroxide, or potassium hydroxide.

The transformation from compound XXXIV to product XXXVI may be accomplished by any of several routes known in the art. See U.S. Pat. No. 3,711,515. Thus, by step (h), the alkene XXXIV is hydroxylated to glycol XXXV. For this purpose osmium tetroxide is a suitable reagent, for example in conjunction with N-methylmorpholine oxidehydrogen peroxide complex (see Fieser et al., "Reagents for Organic Synthesis", p. 690, John Wiley Sons, Inc., New York (1967)). Thereafter, several methods are available for obtaining the formula-XXXVI product. In one method the glycol is converted to a bis(alkanesulfonic acid) ester and subsequently hydrolyzed to XXXVI by methods known in the the art (see, for example German Offenlegungsschrift No. 1,937,676, Derwent Farmdoc 6862R); see also U.S. Pat. No. 3,843,712. Another method is by way of a diformate by formolysis of the glycol (see U.S. Pat. No. 3,711,515).

Still another method is by way of a cyclic ortho ester. For this purpose, glycol XXXV is reacted with an ortho ester of the formula

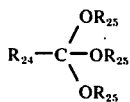

wherein $R_{24}$ is hydrogen, alkyl of one to 19 carbon atoms, inclusive, or aralkyl of 7 to 12 carbon atoms, inclusive, substituted with zero to 3 halo atoms; and $R_{25}$ is methyl or ethyl. There is then formed a cyclic ortho ester of the formula

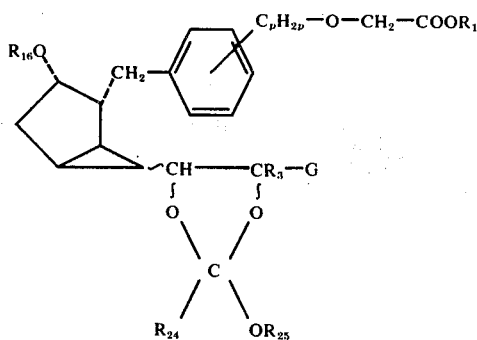

wherein $C_pH_{2p}$, G, $R_1$, $R_3$, $R_{16}$, $R_{24}$, $R_{25}$, and ~ are as defined above. The reaction goes smoothly in a temperature range of −50° C. to +100° C., although for convenience 0° C. to +50° C. is generally preferred. From 1.5 to 10 molar equivalents of the ortho ester are employed, together with an acid catalyst. The amount of the catalyst is usually a small fraction of the weight of the glycol, say 1%, and typical catalysts include pyridine hydrochloride, formic acid, hydrogen chloride, p-toluenesulfonic acid, trichloroacetic acid, or trifluoroacetic acid. The reaction is preferably run in a solvent, for example benzene, dichloromethane, ethyl acetate, or diethyl ether. It is generally completed within a few minutes and is conveniently followed by TLC (thin layer chromatography on basic silica gel plates).

The ortho ester reagents are known in the art or readily available by methods known in the art. See for example S. M. McElvain et al., J. Am. Chem. Soc. 64, 1925 (1942), starting with an appropriate nitrile. Examples of useful ortho esters include:
  trimethyl orthoformate,
  triethyl orthoacetate,
  triethyl orthopropionate,
  trimethyl orthobutyrate,
  triethyl orthovalerate,
  trimethyl orthooctanoate,
  trimethyl orthophenylacetate, and
  trimethyl ortho (2,4-dichlorophenyl)acetate.
Preferred are those ortho esters wherein $R_{24}$ is alkyl of one to 7 carbon atoms; especially preferred are those wherein $R_{24}$ is alkyl of one to 4.

Next, the cyclic orthoester LI is reacted with anhydrous formic acid to yield a diol diester of the formula

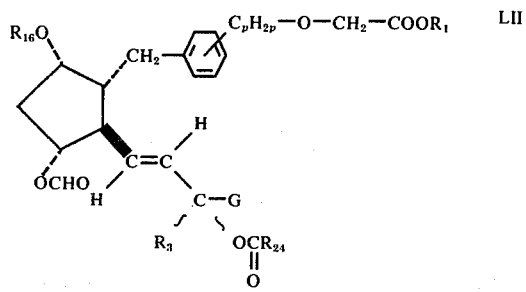

wherein $C_pH_{2p}$, G, $R_1$, $R_3$, $R_{16}$, $R_{24}$, and ~ are as defined above.

By "anhydrous formic acid" is meant that it contains not more than 0.5% water. The reaction is run with an excess of formic acid, which may itself serve as the solvent for the reaction. Solvents may be present, for example dichloromethane, benzene, or diethyl ether, usually not over 20% by volume of the formic acid. There may also be present organic acid anhydrides, for example acetic anhydride, or alkyl orthoesters, for example trimethyl orthoformate, which are useful as drying agents for the formic acid. Although the reaction proceeds over a wide range of temperatures, it is conveniently run at about 20°–30° C. and is usually completed within about 10 minutes.

Finally, the diol diester LII is converted to product XXXVI by methods known in the art, for example by hydrolysis in the presence of a base in an alcoholic medium. Examples of the base are sodium or potassium carbonate or sodium or potassium alkoxides including methoxides or ethoxides. The reaction is conveniently run in an excess of the solvolysis reagent, for example methanol or ethanol. The temperature range is from −50° C. to 100° C. The time for completion of the reaction varies with the nature of $R_{24}$ and the base, proceeding in the case of alkali carbonates in a few minutes when $R_{24}$ is hydrogen but taking up to several hours when $R_{24}$ is ethyl, for example.

When the solvolysis proceeds too long or when conditions are too severe, ester groups at $R_1$ may be removed. They are, however, readily replaced by methods known in the art. For example, the alkyl, cycloalkyl, and aralkyl esters are replaced by interaction of the formula-XXXVI acids with the appropriate diazohydrocarbon. For example, when diazomethane is used, the methyl esters are produced. Similar use of diazoethane, diazobutane, 1-diazo-2-ethylhexane, diazocyclohexane, and phenyldiazomethane, for example, gives the ethyl, butyl, 2-ethylhexyl, cyclohexyl, and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley & Sons, Inc., New York, N.Y., Vol. 8, pp. 389-394 (1954).

An alternative method for esterification of the carboxyl moiety comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The phenyl and substituted phenyl esters are prepared by silylating the acid to protect the hydroxy groups, for example, replacing each —OH with —O—Si—(CH$_3$)$_3$. Doing that may also change —COOH to —COO—Si—(CH$_3$)$_3$. A brief treatment of the silylated compound with water will change —COO—Si—(CH$_3$)$_3$ back to —COOH. Procedures for this silylation are known in the art. Then, treatment of the silylated compound with oxalyl chloride gives the acid chloride which is reacted with phenol or the appropriate substituted phenol to give a silylated phenyl or substituted phenyl ester. Then the silyl groups, e.g., —O—Si—(CH$_3$)$_3$ are changed back to -OH by treatment with dilute acetic acid. Procedures for these transformations are known in the art.

Referring to Chart B, there are shown process steps by which the formula-XXX bicyclo hexane is transformed first to an oxetane XXXVII with a fully developed side chain

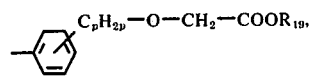

CHART B

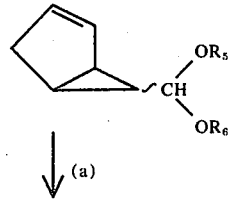 XXX

↓ (a)

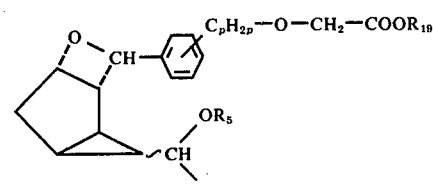 XXXVII

↓ (b)

-continued
CHART B

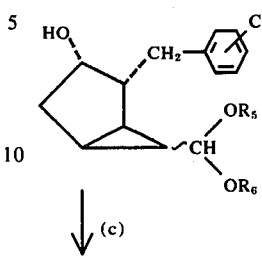 XXXVIII

↓ (c)

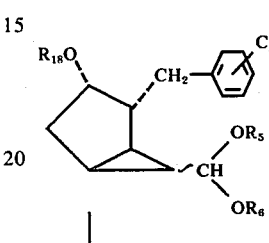 XXXIX

↓ (d)

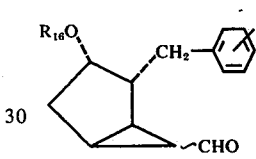 XL

↓ (e)

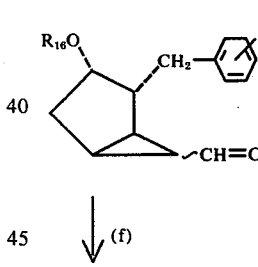 XLI

↓ (f)

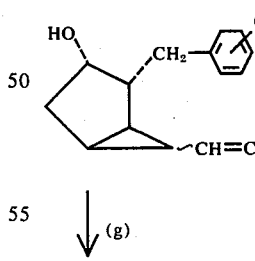 XLII

↓ (g)

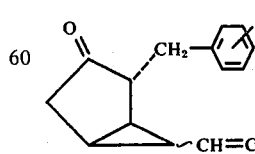 XLIII

↓ (h)

CHART B

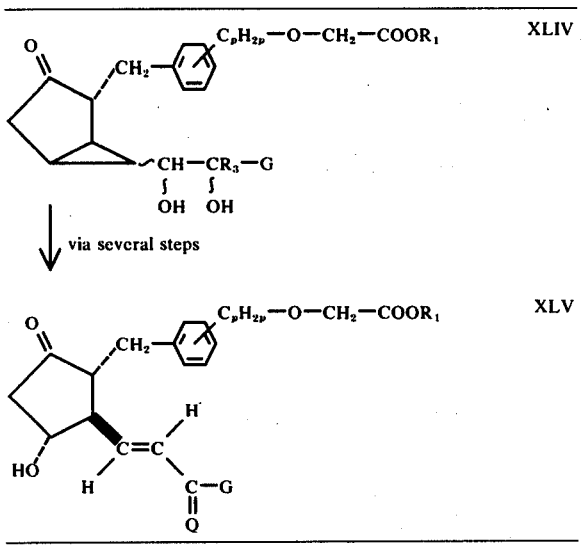

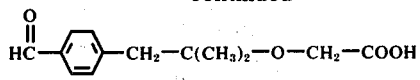

and ultimately to a PGE analog. In Chart B, $R_{19}$ is hydrogen or alkyl of one to 4 carbon atoms, inclusive, and $R_{20}$ is hydrogen, alkyl of one to 4 carbon atoms, inclusive, or silyl of the formula $(A)_3Si$— wherein A is as defined herein above.

In step (a) of Chart B, there is employed an aldehyde of the formula

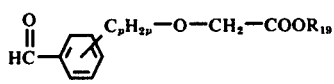

wherein $C_pH_{2p}$ and $R_{19}$ are as defined above. Such aldehydes are available or readily prepared by methods known in the art. Examples of such compounds include:

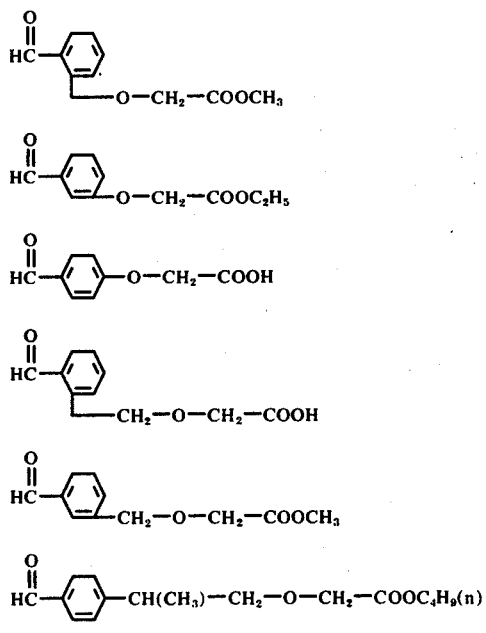

The conditions for step (a) of Chart B are essentially the same as for step (a) of Chart A. Thereafter, step (b) for cleavage of the oxetane ring, steps (c) and (d) leading to the formula-XL aldehyde, and the Wittig reaction of step (e) are similar to and employ the same conditions as the corresponding steps of Chart A discussed above.

Referring to step (g) of Chart B, the hydroxyl on the cyclopentane ring at the C-9 position is oxidized to an oxo group.

Oxidation reagents useful for this transformation are known in the art. A useful reagent for this purpose is the Jones reagent, i.e., acidified chromic acid. See J. Chem. Soc. 39 (1946). A slight excess beyond the amount necessary to oxidize the C-9 secondary hydroxy groups of the formula-XLII reactant is used. Acetone is a suitable diluent for this purpose. Reaction temperatures at least as low as about 0° C. should be used. Preferred reaction temperatures are in the range 0° to −50° C. Another useful reagent for this purpose is the Collins reagent, i.e. chromium trioxide in pyridine. See J. C. Collins et al., Tetrahedron Lett., 3363 (1968). Dichloromethane is a suitable diluent for this purpose. Reaction temperatures of below 30° C. should be used. Preferred reaction temperatures are in the range 0° to +30° C. The oxidation proceeds rapidly and is usually complete in about 5 to 20 minutes.

Examples of other oxidation reagents useful for this transformation are silver carbonate on Celite (Chem. Commun. 1102 (1969)), mixtures of chromium trioxide and pyridine J. Am. Chem. Soc. 75, 422 (1953), and Tetrahedron, 18, 1351 (1962)), t-butychromate in pyridine (Biochem. J. 84, 195 (1962)), mixtures of sulfur trioxide in pyridine and dimethylsulfoxide (J. Am. Chem. Soc. 89, 5505 (1967)), and mixtures of dicyclohexylcarbodiimide and dimethyl sulfoxide (J. Am. Chem. Soc. 87, 5661 (1965)).

Step (h) of Chart B and subsequent steps by which the product XLV is obtained are similar to and employ the same conditions as the corresponding steps of Chart A discussed above.

Referring next to Chart C the process steps are shown whereby aldehyde XXI of Chart A is transformed to a 17,18-tetradehydro-PG analog XXIV and a 17,18-didehydro-PG analog L.

In step (a) of Chart C, a Wittig reagent is employed which is prepared from a phosphonium salt of a haloalkyne of the formula

or

wherein $C_nH_{2n}$, $R_3$, and $R_4$ are as defined above. See, for example, U. Axen et al., Chem. Comm. 1969, 303, and ibid. 1970, 602.

Thereafter, in steps (b) to (d) and subsequent steps yielding the 17,18-tetradehydro compound XXIV, the reagents

CHART C

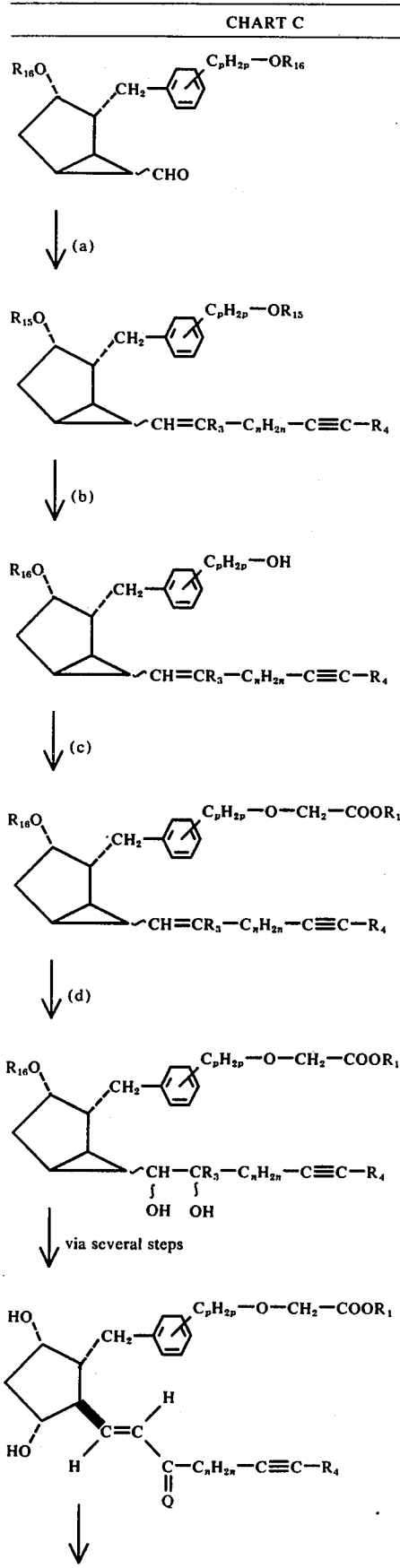

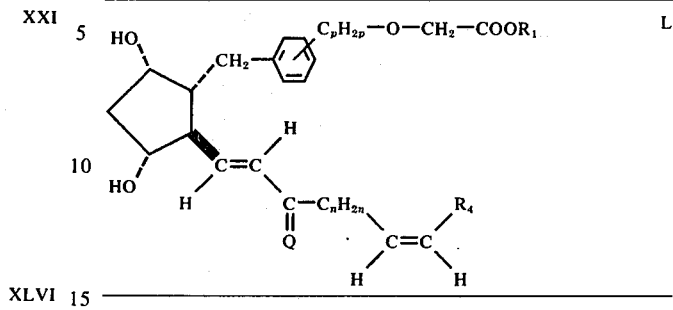

and conditions are similar to those employed for the corresponding reactions shown in Chart A.

Transformation of XXIV to the formula-L compounds is accomplished by hydrogenation of XXIV using a catalyst which catalyzes hydrogenation of $-C\equiv C-$ only to cis-$CH=CH$-, as known in the art. See, for example, Fieser et al., "Reagents for Organic Syntheses", pp. 566—567, John Wiley and Sons, Inc., New York (1967). Preferred is Lindlar catalyst in the presence of quinoline, see Axen, references cited.

Referring next to Chart D there are shown process steps leading to intermediate LVII:

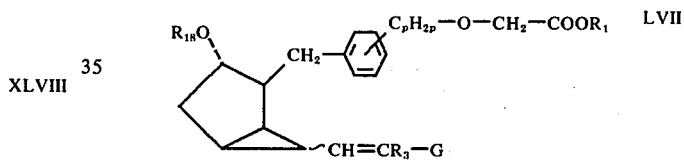

wherein $C_pH_{2p}$, $R_1$, $R_5$, $R_6$, $R_{18}$, and ~ are as defined above for Chart A. Furthermore, in Chart D, G has the same definition as for Charts A, B, and C above.

In step (a) of Chart D, the oxetane ring of compound XX is cleaved by catalytic hydrogenation, for example in the presence of a noble metal catalyst such as palladium on carbon. Useful solvents for such a reaction include lower alkyl alcohols, e.g. methanol, ethanol, isopropanol, and butanol, and their isomers, lower alkyl ethers, e.g. diethyl ether, cyclic ethers, e.g. 1,4-dioxane, esters, e.g. ethyl acetate, hydrocarbons, e.g. benzene, and mixtures thereof. Hydrogen

CHART D

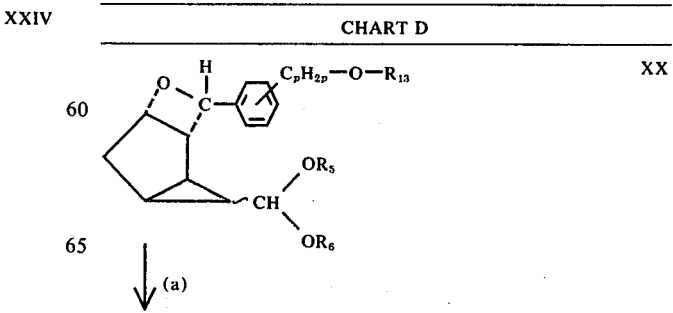

CHART D

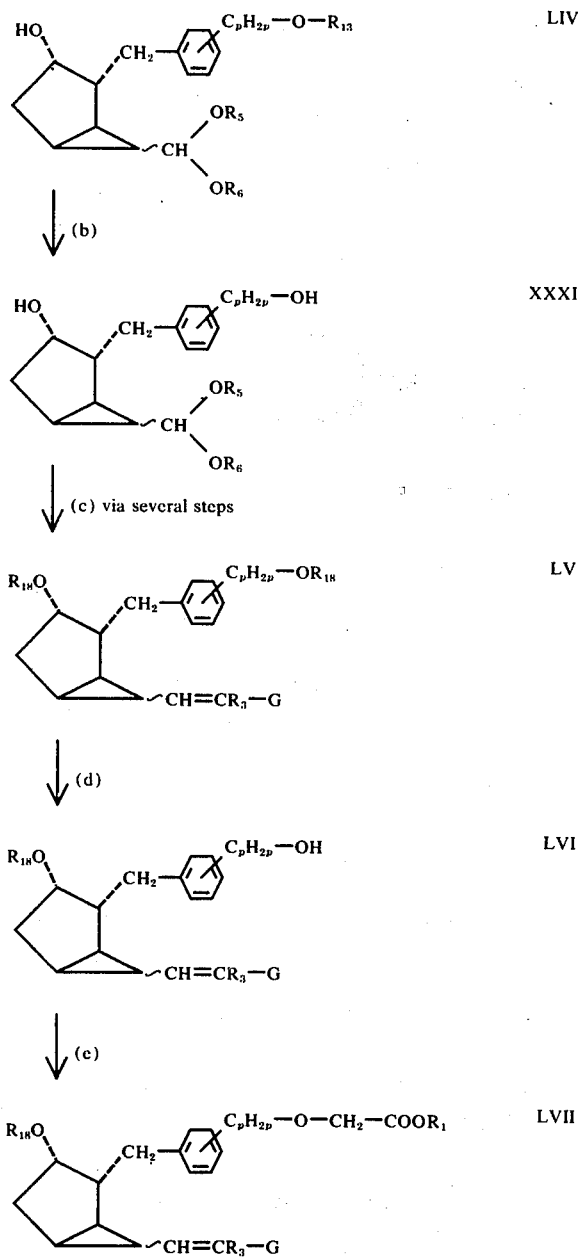

is employed at low pressures, e.g. atmospheric up to 30 psig. Temperatures in the range 10°–40° C. are useful.

In step (b) $R_{13}$ of compound LIV is replaced with hydrogen by hydrolysis in aqueous mixture containing water-miscible solvents such as ethanol, acetone, 1,4-dioxane, or tetrahydrofuran, in the presence of a base such as sodium or potassium carbonate. The carbonate is used preferably in equivalent or slight excess of equivalent amounts. Temperatures in the range −10° to 100° C. are useful.

In step (c), representing several steps, diol XXXI is transformed to compound LV by successively (1) blocking the two hydroxy groups with blocking groups within the scope of $R_{18}$ as defined above for Chart A, using the appropriate acid chloride or anhydride re- agents and conditions described above; (2) converting the

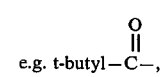

acetal moiety to an aldehyde group by acid hydrolysis discussed for step (d) of Chart A above; and (3) transforming the aldehyde group to a moiety of the formula —CH=CR$_3$G using a Wittig reacton as discussed for step (e) of Chart A above.

In step (d), compound LVI is obtained by deblocking if necessary. When $C_pH_{2p}$ is a valence bond, and $R_{18}$ is a hindered carboxyacyl,

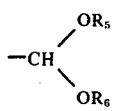

$R_{18}$ on the phenolic hydroxy is selectively replaced with hydrogen by hydrolysis, preferably with the reagents employed for step (b) of Chart D above, but using a temperature range of about −10° to 40° C. At higher temperatures there is some decrease in selectivity.

In step (e) a Williamson synthesis is employed to obtain compound LVII, using reagents discussed above for step (g) of Chart A. When $R_1$ in Hal—CH$_2$—COOR$_1$ is an ester group, the condensing base is preferably a hydride, e.g. sodium, lithium, potassium, or calcium hydride.

Intermediate LVII of Chart D is transformed to intermediate XXXV of Chart A and thence to final products XXXVI by methods disclosed herein or known in the art.

For phenylene compounds, reference to Charts E and F will make clear the steps by which starting material XXX is transformed to products LXXII and LXXV. The formula-XXX compound has been described above for Chart A.

In Charts E and F the symbols Q, $R_1$, $R_3$, $R_{16}$, $R_{18}$, $R_{19}$, $R_{20}$, and ~ have the same meanings as for Charts A-D above.

Referring to Chart E, in step (e) oxetane LXIII is obtained by reaction of the formula-XXX bicyclic hexene with an aldehyde of the formula

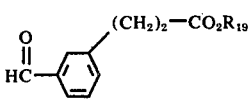

LXXXI wherein $R_{19}$ is hydrogen or alkyl of one to 4 carbon atoms, inclusive. Such aldehydes are available or readily prepared by methods known in the art. Chart G summarizes the steps employed herein (See Preparations CHART E
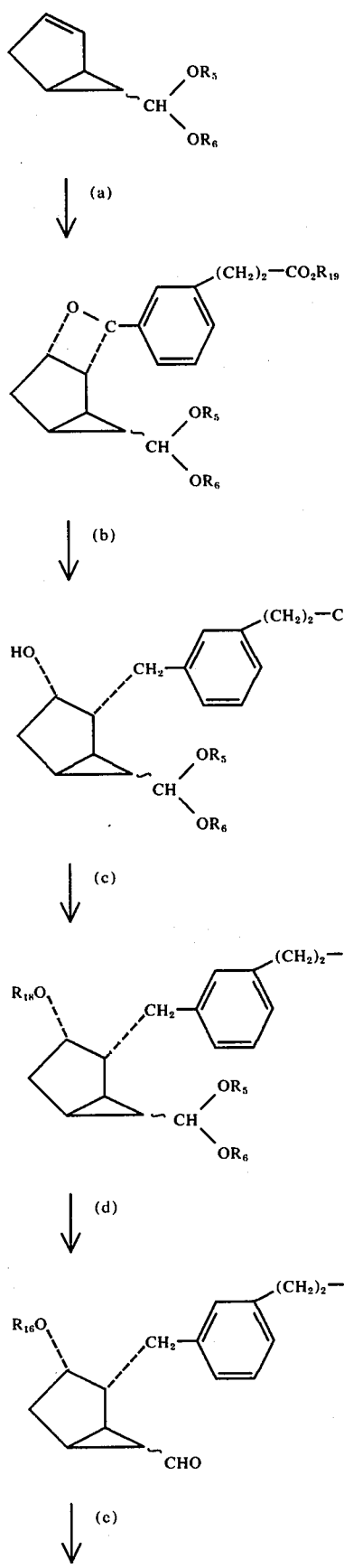
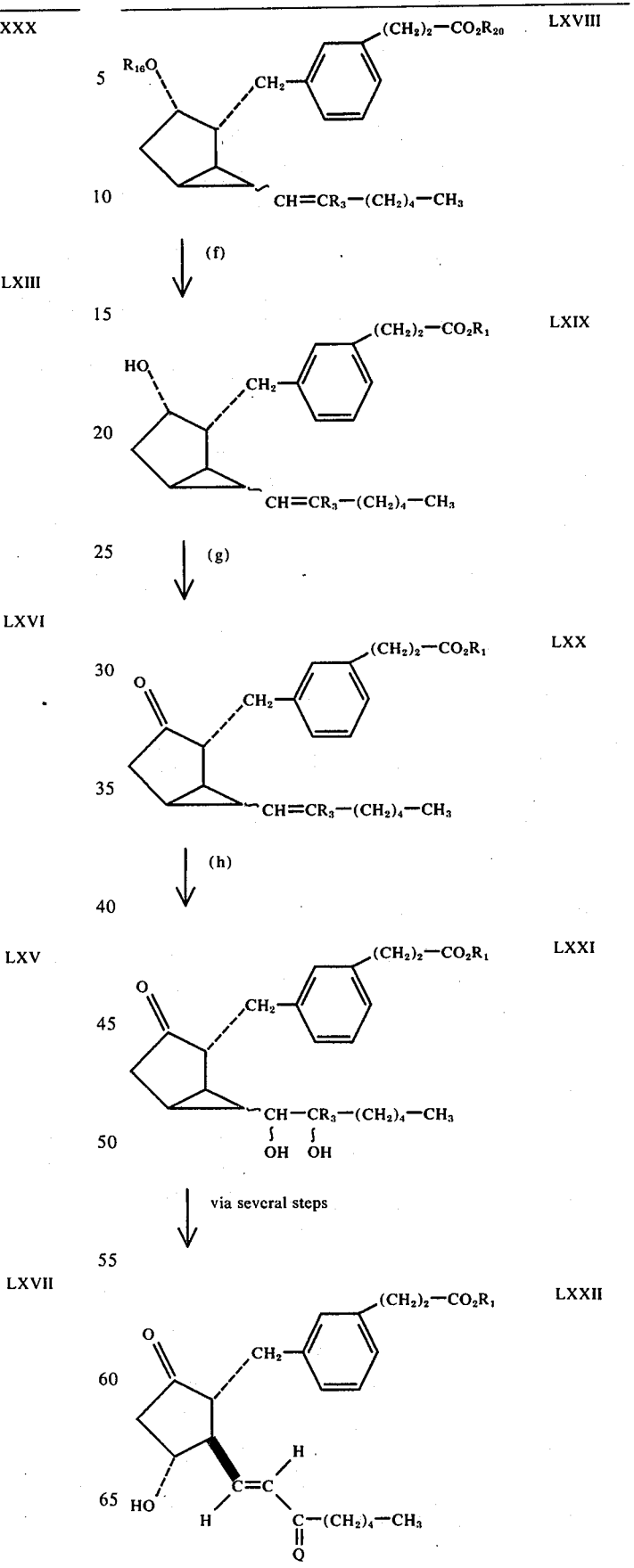

CHART F

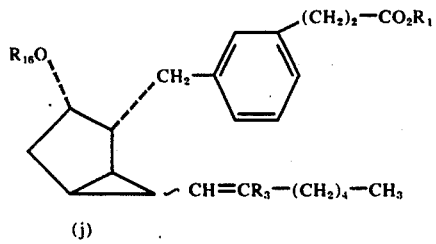
(j)    LXIV

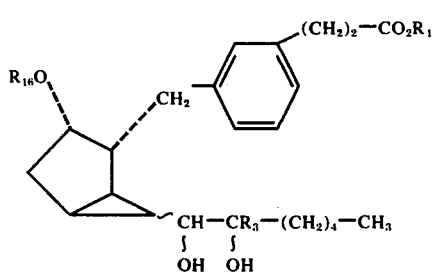
LXXIV via several steps

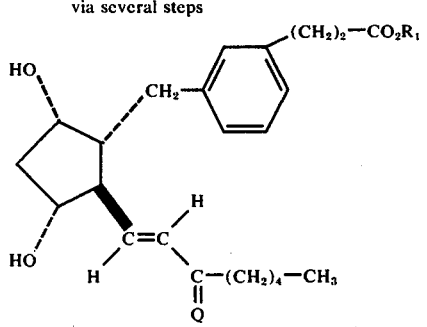
LXXV

CHART G

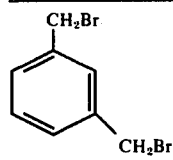
LXXVI

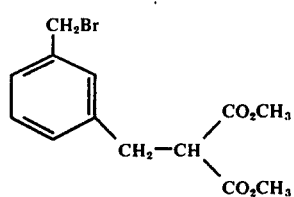
LXXVII

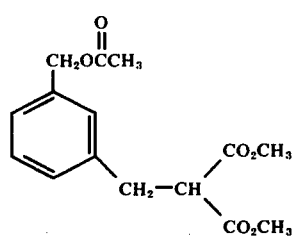
LXXVIII

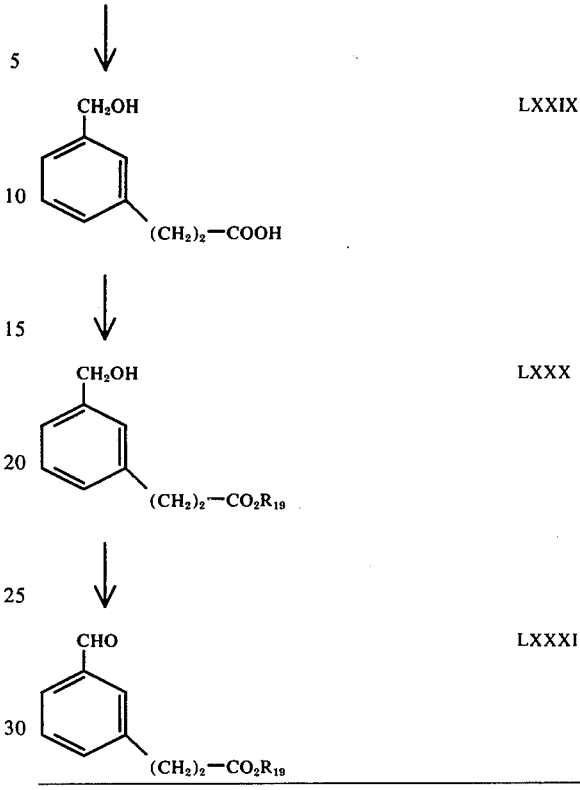

2 – 6 for the preparation of (m-formylphenyl)propionate, methyl ester).

The conditions for the formation of oxetane LXIII are similar to those described above for step (a) of Chart B. Likewise steps (b) through (h) of Chart E to the formula-LXVIII alkene use conditions described above for steps (b) through (h) of Chart B or reactions which are known in the art. Subsequent steps by which the PGE-type products LXXII are obtained are similar to and employ the same conditions as the corresponding steps of Chart B. For this purpose a choice of three methods is given: hydrolysis of a bis(alkanesulfonic acid) ester, formolysis, or by way of a cyclic ortho ester, the first being preferred.

Reference to Chart F will show the steps leading from a formula-LXXXIII alkene, readily available from the formula-LXVIII alkene of Chart E, to the PGF$_1$ -type products of formula LXXV.

The novel intermediates of Charts A, B, C, D, E, and F, including those compounds represented by formulas XX, XXI, XXII, XXIV, XXXI, XXXII, XXXIII, XXXV, XXXIV, XXXVII, XXXVIII, XXXIX, XL, XLI, XLII, XLIII, XLIV, XLVI, XLVII, XLVIII, XLIX, LIV, LV, LVI, LVII, LXIII, LXIV, LXV, LXVI, LXVII, LXVIII, LXX, LXIX, LXXI, XLIII, and LXXIV are frequently not isolated but used directly for subsequent process step. When they are isolated, they are purified by methods known in the art, for example partition extraction, fractional crystalization, and, preferably, silica gel column chromatography.

The products represented by formulas XXXVI, XLV, L, LXXII, and LXXV obtained from these intermediates are often a mixture of 15-α and 15-β isomers. These are separated by methods known in the art, for example, by chromatography on neutral silica gel. In some instances, particularly where $R_3$ is alkyl, the lower alkyl esters are more readily separated than are the corresponding acids. In those cases wherein $R_1$ is hydrogen, it is advantageous to esterify the mixture of acids, as with diazomethane, to form the methyl esters, separate the two epimers, and then, if desired, replace the carboxyl methyl with hydrogen by methods known in the art.

When an optically active intermediate or starting material is employed, subsequent steps yield optically active intermediates or products. That optical isomer of bicyclo hexene XXX is used which will yield product XXXVI, for example, in the configuration corresponding to that of the naturally occurring prostaglandins. When the racemic form of the intermediate or starting material is employed, the subsequent intermediates or products are obtained in their racemic form.

DESCRIPTION OF THE PREFERRED EMBODIMENTS

The invention can be more fully understood by the following examples and preparations:

All temperatures are in degrees centigrade.

Infrared absorption spectra are recorded on a Perkin-Elmer Model 421 infrared spectrophotometer. Except when specified otherwise, undiluted (neat) samples are used.

NMR spectra are recorded on a Varian A-60, A-60D, or T-60 spectrophotometer using deuterochloroform solutions with tetramethylsilane as an internal standard (downfield).

Mass spectra are recorded on a CEC Model 110B Double Focusing High Resolution Mass Spectrometer or an LKB Model 9000 Gas Chromatograph-Mass Spectrometer (ionization voltage 70 ev).

Circular dichroism curves are recorded on a Carey 60 recording spectropolarimeter.

Specific rotations are determined for solutions of a compound in the specified solvent with a Perkin-Elmer Model 141 Automatic Polarimeter.

"Brine", herein, refers to an aqueous saturated sodium chloride solution.

"Skellysolve-B" refers to mixed isomeric hexanes.

Silica gel chromatography, as used herein, is understood to include elution, collection of fractions, and combination of those fractions shown by TLC (thin layer chromatography) to contain the desired product free of starting material and impurities.

PREPARATION 1

Optically Active
Bicyclo[3.1.0]-hex-2-ene-6-endo-carboxaldehyde

Following the procedure of Preparation 1 of U.S. Pat. No. 3,711,515, racemic bicyclo[3.1.0]hex-2-ene-6-endo-carboxaldehyde is prepared from bicyclo[2.2.1]hepta2,5-diene and peracetic acid.

The racemic compound is resolved by the procedure of Example 13 of U.S. Pat. No. 3,711,515, forming an oxazolidine as follows.

Racemic bicyclo[3.1.0]hex-2-ene-6-endo-carboxaldehyde (12.3 g.) and 1-ephedrine (16.5 g.) are dissolved in about 150 ml. of benzene. The benzene is removed under vacuum and the residue is taken up in about 150 ml. of isopropyl ether. The solution is filtered, then cooled to −13° C. to yield crystals of 2-endo-bicyclo[3.1.0]hex-2-en-6-yl-3,4-dimethyl-5-phenyl-oxazolidine, 11.1 g., m.p. 90°–92° C. Three recrystallizations from isopropyl ether, cooling each time to about −2° C., yield crystals of the oxazolidine, 2,2 g., m.p. 100°–103° C., now substantially a single isomeric form as shown by NMR.

The above re-crystallized oxazolidine (1.0 g.) is dissolved in a few ml. of dichloromethane, charged to a 20 g. silica, gel column and eluted with dichloromethane. The silica gel is chromatography-grade (Merck), 0.05–0.2 mm. particle size, with about 4-5 g. of water per 100 g. Fractions of the eluate are collected, and those shown by thin layer chromatography (TLC) to contain the desired compound are combined and evaporated to an oil (360 mg.). This oil is shown by NMR to be the desired title compound, substantially free of the ephedrine, in substantially a single optically-active isomeric form. Points on the circular dichroism curve are ($\lambda$ in nm., $\Theta$): 350, 0; 322.5, −4,854; 312, −5,683; 302.5, −4,854; 269, 0; 250, 2,368; 240, 0; and 210, −34,600.

PREPARATION 2 m-(Bromomethyl)-benzylmalonate, Dimethyl Ester (Formula LXXVII)

Refer to Chart G. A solution of dimethyl malonate (26.42 g.) in 600 ml. of tetrahydrofuran is treated with potassium tertiary butoxide (10.52 g.) for 5 min. at about 25° C. Thereupon $\alpha,\alpha'$-dibromo-m-xylene (25.0 g.) is added and the mixture stirred at ambient temperature for 2.5 hr. The reaction is quenched by addition of 100 ml. of water and 50 ml. of 5% hydrochloric acid. The mixture is extracted with diethyl ether and the extract is washed with water and brine, dried over magnesium sulfate and concentrated to an oil. The crude product is subjected to chromatography on silica gel, eluting with Skellysolve B-ethyl acetate (first 95:5 and then 50:50). Yield of title compound: 31.5 g., having NMR peaks at 3.67, 4.43, and 7.20 $\delta$.

PREPARATION 3 m-(Acetoxymethyl)-benzylmalonate, Dimethyl Ester (Formula LXXVIII)

Refer to Chart G. A mixture of m-(bromomethyl)-benzyl-malonate, dimethyl ester (Preparation 2, 31.5 g.) and potassium acetate (17.5 g.) in 280 ml. of dimethylformamide is heated at 50° C. for about 0.5 hr. until no starting material is shown by TLC (thin layer chromatograhy on silica gel plates, in Skellysolve B-ethyl acetate (75:25). The mixture is taken up in diethyl ether-Skellysolve B (1:1) and washed with water and brine, dried over magnesium sulfate, and concentrated to an oil. The crude product is subject to silica gel chromatography, eluting with Skellysolve B-ethyl acetate (90:10 to 30:70). Yield of title compound: 9.66 g., having infrared absorption at 1740, 1610, 1595, 1490, 1435, 1230, 1155, and 1030 $cm^{-1}$; NMR peaks at 2.08, 3.67, 5.07, and 7.19 $\delta$; and mass spectral peaks at 294, 134, 101, 74, 59, 57, 45, 43, 42, 29, and 15.

PREPARATION 4 m-(Hydroxymethyl)-phenylpropionic Acid (Formula LXXIX)

Refer to Chart G. A solution of m-(acetoxymethyl)-benzylmalonate, dimethyl ester (Preparation 3, 9.16 g.) in 45 ml. of dioxane is treated with 137 ml. of 10% sodium hydroxide at about 25° C. for 15 min. The mixture is acidified to pH 1.0 with sulfuric acid, treated with an additional 3 ml. of sulfuric acid, and heated at reflux for about 36 hr. The mixture is cooled, diluted with 430 ml. brine and extracted with chloroform. The extract is washed with brine, dried over magnesium sulfate, and concentrated. Yield of title compound: 4.31 g., having NMR peaks at 2.40–3.18, 4.58, 7.17, and 7.53 $\delta$.

PREPARATION 5 m-(Hydroxymethyl)-phenylpropionate, Methyl Ester (Formula LXXX, wherein $R_{19}$ is methyl)

Refer to Chart G. A solution of m-(hydroxymethyl)-phenylpropionic acid (Preparation 4, 4.31 g.) in 7.15 ml. of dichloromethane is treated with 2.29 g. of methanol and 0.076 ml. of concentrated sulfuric acid, heated at reflux for 3.0 hr. The mixture is cooled, diluted with brine, and extracted with diethyl ether. The extract is washed with sodium bicarbonate solution and brine, dried over magnesium sulfate, and concentrated to an oil. Yield of title compound: 3.31 g. On subjecting the product to silica gel chromatography, eluting with Skellysolve B-ethyl acetate (75:25 to 35:65), there is recovered 95% of the product in selected fractions, having NMR peaks at 2.37–3.17, 3.60, 4.58, and 7.15 $\delta$.

PREPARATION 6

(m-Formylphenyl)propionate, Methyl Ester (Formula LXXXI, wherein $R_{19}$ is methyl)

Refer to Chart G. A mixture of m-(hydroxymethyl)-phenylpropionate, methyl ester (Preparation 5, 3.72 g.) and 40.92 ml. of 1M. ceric ammonium nitrate solution in 40.92 ml. of acetic acid is stirred at 65° C. for 2 hr. Then another 2 ml. of ceric ammonium nitrate solution is added and treatment continued at 65° C. for one hr. The mixture is cooled, diluted with brine and extracted with diethyl ether. The ether extract is washed with brine and water, dried over sodium sulfate, and concentrated to an oil.

The above product, containing the acid, is converted to the title compound with diazomethane. The mixture is quenched with 10% acetic acid, diluted with brine, and extracted with diethyl ether. The ether extract is washed with sodium bicarbonate solution and brine, dried, and concentrated to the title compound, 2.90 g. Taking additional material, the combined lot (4.48 g.) is subjected to silica gel chromatography, eluting with Skellysolve B-ethyl acetate (90:10 to 60:40) to yield 3.532 g., b.p. 0.35 mm. 105°–107° C. and having NMR peaks at 2.50-3.28, 3.65, 7.17-7.93. and 10.00 $\delta$; mass spectral peaks at 192, 161, 133, 132, 131, 119, 105, 103, 77 and 51; and infrared absorption bands at 3000, 2940, 2840, 2720, 1735, 1700, 1605, 1585, 1485, 1435, 1295, 1240, 1200, 1160, 1145, 795, 690, and 650 cm$^{-1}$; and $R_f$ 0.36 (TLC on silica gel in 25% ethyl acetate-Skellysolve B).

EXAMPLE 1

1 3.1.0]hex-2-ene-6-endo-carboxaldehyde Neopentyl Glycol Acetal (Formula XXX: $R_5$ and $R_6$ taken together are —$CH_2$-$C(CH_3)_2$—$CH_2$—and $\sim$ is endo)

A mixture of 2,2-dimethyl-1,3-propanediol (900 g.), 5 l. of benzene and 3 ml. of 85% phosphoric acid is heated at reflux. To it is added, in 1.5 hr., a solution of optically active bicyclo[3.1.0]hex-2-ene-6-endo-carboxaldehyde (Prep. 1, 500 g.) in one liter of benzene. Provison is made to take off azeotropically distilled water with a Dean-Stark trap. After 3 hr. the mixture is cooled and extracted with 2 liters of 5% sodium bicarbonate. The organic phase is dried over sodium sulfate and concentrated under reduced pressure. The resulting semisolid residue is taken up in methanol and recrystallized, using a total of 1200 ml. of methanol to which 600 ml. of water is added, then chilled to −13° C. to yield 300 g. of the title compound, m.p. 52°–55° C., and having NMR peaks at 0.66, 1.20, 0.83–2.65, 3.17–3.8, 3.96, and 5.47–5.88 $\delta$, $[\alpha]_D$ − 227° (C=0.8976 in methanol), and $R_f$ 0.60 (TLC on silica gel in 25% ethyl acetate in mixed isomeric hexanes). Further work-up of the mother liquors yields 50-100 g. of additional product.

Following the procedures of Example 1 but replacing the aldehyde with optically active bicyclo[3.1.0]hex-2-ene-6-exo-carboxaldehyde (see U.S. Pat. No. 3,711,515), there is obtained the corresponding formula-XXX acetal.

Following the procedures of Example 1 but using either the endo or exo form of the aldehyde and substituting for 2,2-dimethyl-1,3-propanediol one of the following glycols: ethylene glycol, 1,2-propanediol, 1,2-hexanediol, 1,3-butanediol, 2,3-pentanediol, 2,4-hexanediol, 2,4-octanediol, 3,5-nonanediol, 3,3-dimethyl-2,4-heptanediol, 4-ethyl-4-methyl-3,5-heptanediol, phenyl-1,2-ethanediol and 1-pentyl-1,2-propanediol, there are obtained the corresponding formula-XXX acetals.

EXAMPLE 2 d-8-(m-Acetoxyphenyl)-7-oxa-tricyclo-[4.2.0.0$^{2,4}$]oc-tane-6-endo-carboxaldehyde Neopentyl Glycol Acetal (Formula XX: $C_nH_{2p}$ is a valence bond with attachment in the meta position, $R_5$ and $R_6$ taken together are -$CH_2$-$C(CH_3)_2$-$CH_2$-, $R_{13}$ is

and $\sim$ is endo)

Refer to Chart A, step (a). A solution of the formula-XXX 1-bicyclo[3.1.0]hex-2-ene-6-endo-carboxaldehyde neopentyl glycol acetal (Example 1, 5.82 g.) and m-acetoxy-benzaldehyde(1.64 g.) in 25 ml. of benzene is charged to a Pyrex photolysis vessel equipped with an immersible water-cooled cold-finger and a fritted gas inlet tube. Dissolved oxygen is removed by bubbling nitrogen through the solution. The mixture is then irradiated at 350 nm. with a Rayonet Type RS Preparative Photochemical Reacter (The Southern New England Ultraviolet Co., Middletown, Conn.) equipped with six RUL 3500 A lamps. After 24 hr. the photolysate is concentrated under reduced pressure to a pale yellow oil, 10 g., which is subjected to silica gel chromatography. Elution with 10–70% ethyl acetate in Skellysolve B (mixture of isomeric hexanes) yields separate fractions of the recovered starting materials and the formula-XX title compound, a pale yellow oil, 0.86 g., having NMR peaks at 0.68, 1.20, 0.8-2.5, 2.28, 2.99, 3.12–3.88, 3.48, 4.97–5.52, and 6.78–7.60 $\delta$; infrared absorption bands at 3040, 2950, 2860, 2840, 1765, 1610, 1590, 1485, 1470, 1370, 1205, 1115, 1020, 1005, 990, 790, and 700 cm$^{-1}$; mass spectral peaks at 358, 357, 116, 115, 108, 107, 79, 70, 69, 45, 43, and 41; $[\alpha]_D$ +55° (C=0.7505 in 95% ethanol); and $R_f$ 0.18 (TLC on silica gel in 25% ethyl acetate in mixed isomeric hexanes).

Following the procedures of Example 2 but replacing the formula-XXX acetal with the formula-XXX compounds disclosed following Example 1, there are obtained the corresponding formula-XX compounds in their endo or exo forms and with correponding exemplification of $R_5$ and $R_6$.

Likewise following the procedures of Example 2 but replacing m-acetoxybenzaldehyde with aldehydes within the scope of formula XXVI above, as to $C_pH_{2p}$, the attachment position on the phenyl ring, and the carboxyacyl group $R_{13}$, or defined above, the corresponding formula-XX oxetanes are obtained wherein ~ is endo or exo, and $R_5$ and $R_6$ correspond to the glycols employed after Example 1 above. Specifically, the following formula-XXVI aldehydes are employed:

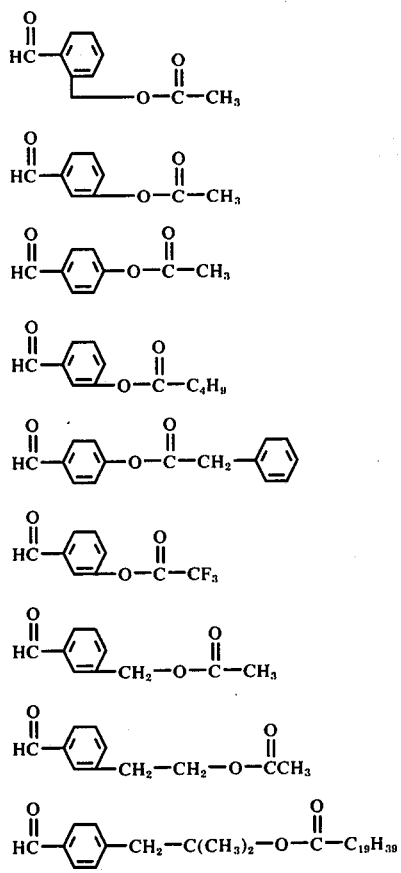

EXAMPLE 3 d-2-Exo-[m-(pivaloyloxy)benzyl]-3-exo-(pivaloyloxy)-bicyclo[3.1.0]hexane-6-endocarboxaldehyde Neopentyl Glycol Acetal(Formula XXXII: $C_pH_{2p}$ is a valence bond with attachment in the meta position, $R_5$ and $R_6$ taken together are —$CH_2$—$C(CH_3)_2$—$CH_2$—, $R_{18}$ is

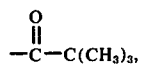

and ~ is endo)

(I). Refer to Chart A, steps (b) and (c). A mixture of lithium (0.25 g.) in 70 ml. of ethylamine is prepared at 0° C. and cooled to −78° C. A solution of the formula-XX d-8-(m-acetoxyphenyl)-7-oxa-tricyclo[4.2.0.0.$^{2,4}$]-octane-6-endo-carboxaldehyde neopentyl glycol acetal (Example 2, 1.83 g.) in 10 ml. of tetrahydrofuran is added dropwise in about 5 min. After stirring at −78° C. for about 3.5 hr. the reaction is quenched with solid ammonium chloride and water-tetrahydrofuran. Unreacted lithium is removed, the mixture is warmed slowly to about 25° C., and ethylamine is removed. The residue is neutralized with dilute acetic acid, mixed with 200 ml. of brine, and extracted with ethyl acetate. The organic phase is washed with brine and a mixture of brine and saturated aqueous sodium bicarbonate (1:1), and dried over sodium sulphate. Concentration under reduced pressure yields the formula-XXXI diol as a pale tan foamed oil, 1.64 g., having $R_f$ 0.03 (TLC on silica gel in 25% ethyl acetate in mixed isomeric hexanes).

(II). The product of part (I) is dissolved in 30 ml. of pyridine and treated with 1.5 ml. of pivaloyl chloride over a period of 22 hr. at about 25° C. The reaction mixture is mixed with water, then brine and extracted with ethyl acetate. The organic phase is washed successively with brine, water, saturated aqueous copper (II) sulfate, saturated aqueous sodium bicarbonate, and brine, and dried over sodium sulfate. Concentration under reduced pressure yields a residue, 2.53 g., which is subjected to silica gel chromatography to yield the formula-XXXII title compound, 1.87 g., having NMR peaks at 0.71, 1.20, 1.33, 0.9–3.1, 3.28–4.00, 4.17, 4.7–5.2, and 6.77–7.53 δ; mass spectral peaks at 486, 485, 115, 73, 72, 57, 44, 43, 42, 41, 30, 29, 15; $[\alpha]_D$ +19° (C=0.9340 in ethanol); $R_f$ 0.50 (TLC on silica gel in 25% ethyl acetate in mixed isomeric hexanes); and m.p. 107.1°–112.2° C.

EXAMPLE 4 d-2-Exo-(m-acetoxybenzyl)-3-exo-acetoxybicyclo[3.1.0]hexane-6-endo-carboxaldehyde Neopentyl Glycol Acetal (Formula XXXII: $C_pH_{2p}$ is a valence bond with attachment in the meta position, $R_5$ and $R_6$ taken together are —$CH_2$—$C(CH_3)_2$—$CH_2$—, $R_{18}$ is

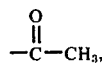

and ~ is endo)

Following the procedures of Example 3-(II) but replacing pivaloyl chloride with acetic anhydride, and using 1.01 g. of the formula-XXXI diol, there is obtained the title compound, 0.75 g., having NMR peaks at 0.72, 1.22, 1.98, 2.27, 0.8–3.0, 3.28–3.85, 4.17, 4.75–5.22, and 6.8–7.47 δ; mass spectral peaks at 402, 401, 115, 107, 73, 69, 45, 44, 43, 42, 41, 30;$[\alpha]_D$ +7° (C=0.7060 in ethanol); and $R_f$ 0.66 (TLC on silica gel in 50% ethyl acetate in mixed isomeric hexanes).

EXAMPLE 5

2-Exo-[m-(pivaloyloxy)benzyl]-3-exo-(pivaloyloxy)-bicyclo[3.1.0]hexane-6-endo-carboxaldehyde (Formula XXI: $C_pH_{2p}$ is a valence bond with attachment in the meta position, $R_{16}$ is

and ~ is endo)

Refer to Chart A, step (d). The formula-XXXII acetal, i.e. d-2-exo-[m-(pivaloyloxy)benzyl]-3-exo-(pivaloyloxy)-bicyclo[3.1.0]hexane-6-endo-carboxaldehyde neopentyl glycol acetal (Example 3, 0.48 g.) is treated at 0° C. with 25 ml. of 88% formic acid for 4 hr. The mixture is diluted with 200 ml. of brine and extracted with ethyl acetate. The organic phase is washed with brine and saturated aqueous sodium bicarbonate, and dried over magnesium sulfate. Concentration under reduced pressure yields an oil, 0.55 g., which is subjected to silica gel chromatography. Elution with 5–15% ethyl acetate in Skellysolve B yields the formula-XXI title compound as an oil, 0.37 g., having NMR peaks at 1.20, 1.33, 0.6–3.2, 5.1–5.5, 6.6–7.5, and 9.73 δ; and $R_f$ 0.50 (TLC on silica gel in 25% ethyl acetate in mixed isomeric hexanes).

EXAMPLE 6

2-Exo-[m-(pivaloyloxy)benzyl]-3-exo-(pivaloyloxy)-6-endo-(cis-1-heptenyl)-bicyclo[3.1.0]hexane (Formula XXII: $C_pH_{2p}$ is a valence bond with attachment in the meta position, G is n-pentyl, $R_{16}$ is

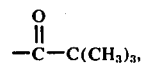

$R_3$ is hydrogen, and ~ is endo); and
2-Exo-(m-hydroxybenzyl)-3-exo-hydroxy-6-endo-(cis-1-heptenyl)bicyclo[3.1.o]hexane (Formula XXXIII: $C_pH_{2p}$ is a valence bond in the meta position, G is n-pentyl, $R_3$ and $R_{16}$ are hydrogen, and ~ is endo)

(I). Refer to Chart A, steps (e) and (f). The Wittig ylid reagent is prepared in 10 ml. of benzene from n-hexyltriphenylphosphonium bromide (0.79 g.) and n-butyllithium (0.6 ml. of 2.32 M. solution in hexane) at about 25° C. for 0.5 hr. After the precipitated lithium bromide has settled, the solution is removed and added to a cold (0° C.) slurry of the formula-XXI aldehyde (Examples 5, 0.37 g.). After 15 min. there is added 1.0 ml. of acetone and the mixture is heated to 60° C. for 10 min. The mixture is concentrated under reduced pressure. The residue is washed with 10% ethyl acetate in Skellysolve B and these washings are concentrated to the formula-XXII title compound, an oil, 0.33 g. having NMR peaks at 1.18, 1.33, 0.6–3.2, 4.5–6.0 and 6.67–7.62 δ; and $R_f$ 0.78 (TLC on silica gel in 25% ethyl acetate in Skellysolve B).

(II). The above product of part (I) is transformed to the formula-XXXIII diol by treatment with sodium methoxide (2.5 ml. of a 25% solution in methanol) for 4 hrs., followed by addition of 0.5 g. of solid sodium methoxide and further stirring for 15 hr. at 25° C., then at reflux for 6 hr. The mixture is cooled, mixed with 300 ml. of brine, and extracted with ethyl acetate. The organic phase is washed with brine, dried over magnesium sulfate, and concentrated under reduced pressure to a residue, 0.27 g. The residue is subjected to silica gel chromatography, eluting with 25–35% ethyl acetate in Skellysolve B, to yield the formula-XXXIII title compound as an oil, 0.21 g., having NMR peaks at 0.87, 0.6–3.25, 3.88–4.35, 4.82–5.92, and 6.47–7.33 δ; and $R_f$ 0.13 (TLC on silica gel in 25% ethyl acetate in Skellysolve B).

Following the procedures of Examples 3, 5, and 6 but replacing the formula XX oxetane with each of those obtained following Example 2, there are obtained successively the corresponding formula-XXXI, -XXXII, -XXI, and -XXII compounds wherein $C_pH_{2p}$ and its attachment position on the phenyl ring correspond to the specific aldehydes employed following Example 2. These are obtained in both their endo and exo forms.

Further following the procedures of Example 6, but replacing the Wittig ylid reagent with one prepared from a compound of the formula

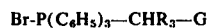

wherein —$CHR_3$-G is each of the following:
—$(CH_2)_3$—$CH_3$
—$(CH_2)_4$—$CH_3$
—$(CH_2)_6$—$CH_3$
—$(CH_2)_7$—$CH_3$
—$CH(CH_3)$—$(CH_2)_5$—$CH_3$
—$CH_2$—$CH(CH_3)$—$(CH_2)_3$—$CH_3$
—$CH_2$—$C(CH_3)_2$—$(CH_2)_3$—$CH_3$
—$CH(CH_3)$—$C(C_2H_5)_2$—$(CH_2)_3$—$CH_3$
—$CH_2$—$CHF$—$(CH_2)_3$—$CH_3$
—$CH_2$—$CF_2$—$(CH_2)_3$—$CH_3$
—$CH(CH_3)$—$CF_2$—$(CH_2)_3$—$CH_3$

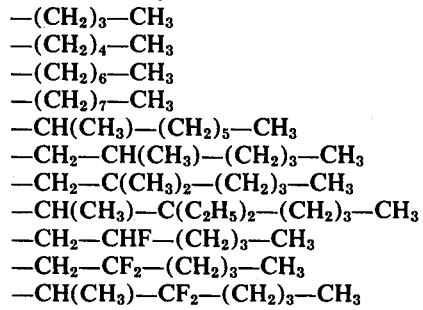

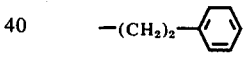

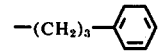

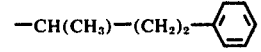

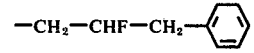

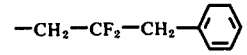

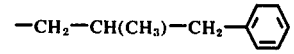

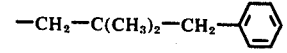

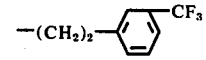

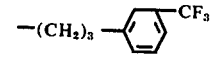

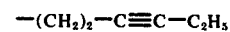

-continued

—$CH_2$—$CH(CH_3)$—$C\equiv C$—$C_2H_5$

—$(CH_2)_2$—$C\equiv C$—$C_2H_5$

—$CH_2$—$CH(CH_3)$—$C\equiv C$—$C_2H_5$ or

—$CH(CH_3)$—$CH_2$—$C\equiv C$—$C_2H_5$ there are obtained the corresponding compounds within the scope of formula XXII wherein $C_pH_{2p}$ and its attachment to the phenyl ring correspond to the specific compounds of Example 6 and those illustrated in the paragraph immediately thereafter, in both their endo and exo forms.

EXAMPLE 7

2-Exo-{m-[(carboxy)methoxy]}-3-exo-hydroxy-6-endo-(cis-1-heptenyl)bicyclo[3.1.0]hexane (Formula XXXIV: $C_pH_{2p}$ is a valence bond with attachment in the meta position, G is n-pentyl, $R_1$, $R_3$, and $R_{16}$ are hydrogen, and ~ is endo)

Refer to Chart A, step (g). The formula-XXXIII diol, i.e. 2-exo-(m-hydroxybenzyl)-3-exo-hydroxy-6-endo-(cis-1-hepentyl)bicyclo[3.1.0]hexane (Example 6, 0.19 g.) is treated in 8 ml. of dioxane with bromoacetic acid (0.61 g.) and 6ml. of 1N. aqueous sodium hydroxide. After the mixture has been heated at reflux for 3 hr., with sodium hydroxide solution added when necessary to maintain a pH of about 10, the mixture is cooled, diluted with 100 ml. of water, and extracted with diethyl ether. The aqueous phase is acidified to pH 1-2 and extracted with ethyl acetate to yield the formula-XXXIV title compound, a pale yellow oil, 0.20 g. Recovered formula-XXXIII diol is obtained from the diethyl ether organic phase on drying and concentrating, 0.025 g.

EXAMPLE 8

3-Oxa-3.7-inter-m-phenylene-4,5,6-trinor-PGF$_1^\alpha$ (Formula VIII: $C_pH_{2p}$ is a valence bond with attachment in the meta position, $R_2$ is n-pentyl, and $R_1$ and $R_3$ are hydrogen)

(I). Refer to Chart A. The formula-XXXIV alkene is transformed to the title compound applying the procedures disclosed in U.S. Pat. No. 3,711,515. Thus, compound XXXIV (Example 7) is hydroxylated by the procedures of Example 6 of that patent to the formula-XXXV glycol of Chart A, using osmium tetroxide either alone or in combination with N-methylmorpholine oxide-hydrogen peroxide complex.

The glycol is then either (1) sulfonated, for example to yield the bismesylate, and then hydroyzed to a mixture of the title compound and its 15-epimer, applying the procedures of Example 7 of that patent, or (2) treated with substantially 100% formic acid to form the diformate of VIII and thereafter hydroyzed to a mixture of the title compound and its 15 epimer, applying the procedures of Examples 20 and 21 of that patent. The epimers are separated by silica gel chromatography to yield the title compound and its 15-epimer.

(II). A third route from glycol XXXV to the title compound is by way of a cyclic ortho ester

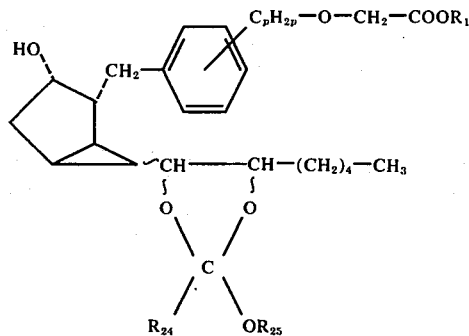

wherein $C_pH_{2p}$, $R_{24}$, $R_{25}$ and ~ are as defined above. The glycol XXXV is treated as a 1-20% solution in benzene with trimethyl orthoformate (1.5-10 molar equivalents) and a catalytic amount (1% of the weight of the glycol) of pyridine hydrochloride at about 25° C. The reaction is followed by TLC (thin layer chromatography) and is complete in a few minutes. There is thus obtained the formula-LI cyclic ortho ester in 100% yield.

The cyclic ortho ester is then treated with 20 volumes of 100% formic acid at about 25° C. In about 10 min. the reaction mixture is quenched in water or aqueous alkaline bicarbonate solution and extracted with dichloromethane. The organic phase is shaken with 5% aqueous sodium bicarbonate, dried over sodium sulfate, and concentrated to yield the formula LII diester, in this example identical with the diformate of compound VIII. The diformate is contacted with 10-50 volumes of anhydrous methanol and 10-20% of its weight of potassium carbonate at about 25° C. until the formyl groups are removed. The mixture of 15-epimers thus obtained is then separated to yield the formula VIII title compound and its 15-epimer.

Following the procedures of Example 8, each of the formula-XXXIV alkenes disclosed following Example 7 is converted into the corresponding phenylene-oxa PGF$\alpha$ analog and its 15-epimer. There are likewise formed the corresponding phenylene oxa 17,18-didehydro-PGF$\alpha$ analogs as shown in Chart C.

EXAMPLE 9

2-Exo-[m-(carboxymethoxy)benzyl]-3-exo-hydroxy-6-endo-(cis-1-heptenyl)bicyclo-[3.1.0]hexane (Formula XLII: $C_pH_{2p}$ is a valence bond with attachment in the meta position, G is n-pentyl, $R_1$ and $R_3$ are hydrogen, and ~ is endo)

Refer to Chart B, steps (a)-(f). There is first prepared the formula-XXXVII oxetane. Following the procedures of Examples 1 and 2, but replacing the m-acetoxybenzaldehyde of Example 2 with an aldehyde within the scope of

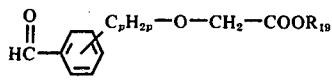   LIII as to $C_pH_{2p}$, the attachment position on the phenyl ring, and the carboxyl group $R_{19}$, as defined above, the corresponding formula XXXVII oxetanes are obtained with a fully developed side chain. Specifically, the following formula-LIII aldehydes are employed:

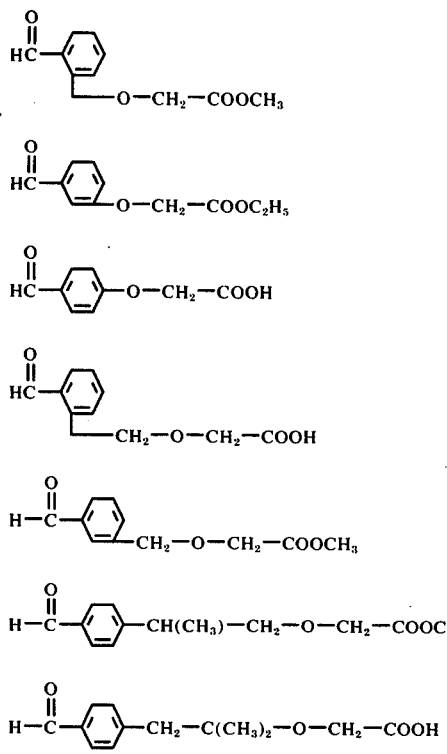

Thereafter, following the procedures of Examples 3, 5, and 6, but replacing the formula-XX octane of Example 3 with those obtained by the procedure disclosed in the above paragraph of this example, there are obtained the corresponding formula-XLI products. Likewise following those procedures of Examples 3, 5, and 6 but replacing the Wittig ylid reagent of Example 6 with one disclosed after Example 6, and applying it to each of the above formula-XX compounds of this example, there are obtained the corresponding formula-XLI compounds with those specific sidechains.

Finally, the blocking groups on each XLI compound are removed by methods disclosed herein or known in the art to yield the formula-XLII title compound and the corresponding formula-XLII compounds from those formula-XLI compounds above.

EXAMPLE 10

2-Exo-{m-[(methoxycarbonyl)methoxy]benzyl}-3-exo hydroxy-6-endo-(cis-1-heptenyl)bicyclo[3.1.0]hexane (Formula XLII: $C_pH_{2p}$ is a valence bond with attachment in the meta position, G is n-pentyl, $R_1$ is methyl, $R_3$ is hydrogen, and ~ is endo)

Refer to Chart B. The formula-XLII acid (Example 7, 0.20 g.) is treated in methanol solution at 0° C. with a solution of diazomethane in diethyl ether (prepared from N-methyl-N-nitroso-N'-nitroguanidine (2.0 g.) and potassium hydroxide (6 ml. of 40% aqueous solution)) unitl a permanent yellow color is produced, and the mixture is concentrated to yield the title compound, a pale tan oil.

EXAMPLE 11

1-6-Endo-(cis-1-heptenyl)-2-exo-{m-[(methoxycarbonyl)methoxy]benzyl}bicyclo[3.1.0]hexan-3-one (Formula XLIII: $C_pH_{2p}$ is a valence bond with attachment in the meta position, G is n-pentyl, $R_1$ is methyl, $R_3$ is hydrogen, and ~ is endo)

Refer to Chart B, step (g). The formula-XLII methyl ester is oxidized to the bicyclic hexanone as follows. The formula-XLII methyl ester (example 8, 0.21 g.) is added in 2 ml. of dichloromethane to a solution of Collins reagent (prepared from pyridine (0.53 g.) and chromium trioxide (0.34 g.) in 10 ml. of dichloromethane) at about 25° c. for 15 min. The mixture is then shaken with a mixture of 60 ml. of diethyl ether, ice, and 25 ml. of 1 N. aqueous sodium hydroxide, and the organic phase is separated. The organic phase is washed with 1 N. aqueous sodium hydroxide, 1.2 N. aqueous hydrochloric acid, and brine, dried, and concentrated under reduced pressure. The residue, a colorless oil, 0.19 g., is subjected to silica gel chromatography, eluting with 5-20% ethyl acetate in Skellysolve B. There is thus obtained the formula-XLIII title compound, a colorless oil, 0.13 g., having NMR peaks at 0.87, 0.6–3.3, 3.77, 4.60, 4.5–5.1, 5.37–5.95, and 6.58–7.40δ; $[\alpha]_D$ −39° (C=0.8380 in 95% ethanol); and $R_f$ 0.42 (TLC on silica gel in 25% ethyl acetate in Skellysolve B).

Following the procedures of Examples 10 and 11, each of the above-identified formula-XLII compounds following Example 9 is oxidized to the corresponding formula-XLIII compound.

EXAMPLE 12

3-Oxa-3,7-inter-m-phenylene-4,5,6-trinor-PGE$_1$, Methyl Ester (Formula IV: $C_pH_{2p}$ is a valence bond with attachment in the meta position, $R_1$ is methyl, $R_2$ is n-pentyl, and $R_3$ is hydrogen)

Following the procedures of Example 8, the formula-XLIII alkene is transformed in several steps to the title compound.

Likewise, following the same procedures, each of the formula-XLIII alkenes disclosed following Example 11 is converted into the corresponding phenylene-oxa PGE analog and its 15-epimer.

Following the procedures of Examples 1–12, each of the endo intermediates is replaced by the corresponding exo intermediate to yield the corresponding exo intermediate or the ultimate phenylene-oxa PG analog.

Likewise following the procedures of Examples 1–12, each of the optically active isomers is replaced by the corresponding racemic mixture to yield the corresponding racemic intermediate or ultimate phenylene-oxa PG analog.

EXAMPLE 13 d-2-Exo(m-acetoxybenzoyl)-3-exo-hydroxybicyclo[3.1.0]hexane-6-endo-carboxaldehyde Neopentyl Glycol Acetal (Formula LIV: $C_pH_{2p}$ is a valence bond with attachment in the meta position, $R_5$ and $R_6$ taken together are —CH$_2$—C(CH$_3$)$_2$—CH$_2$—, $R_{13}$ is acetyl, and ~ is endo)

Refer to Chart D, step (d). A mixture of the formula-XX d-8-(m-acetoxyphenyl)-7-oxa-tricyclo[4.2.0.0$^{2,4}$]octane-6-endo-carboxaldehyde neopentyl glycol acetal (Example 2, 0.36 g.), 10 ml. of ethyl acetate, 5 ml. of absolute ethanol, and 0.25 g. of 10% palladium-on-carbon is shaken with hydrogen at one atmospheric pressure until one equivalent of hydrogen is consumed. The mixture is filtered and the filtrate concentrated under reduced pressure to yield the title compound, 0.36 g. An analytical sample is obtained by subjecting the product to silica gel chromatography: m.p. 122.2°–125.9° C.; $[\alpha]_D^{25}$ +31° (C. 0.9188 in ethanol); $R_f$ 0.22 (TLC on silica gel in ethyl acetatemixed isomeric hexanes (1:1)); NMR peaks at 0.72, 1.23, 2.28, 3.23–3.83, 3.98–4.35, and 6.73–7.48 δ; and mass spectral peaks at 360, 256, 214, 211, 125, 115, 108, 107, 69, 45, 43, and 41.

EXAMPLE 14 d-2-Exo-[m-pivaloyloxy)benzyl]-3-exo(pivaloyloxy)-bicyclo[3.1.0]hexane-6-endo-carboxaldehyde Neopentyl Glycol Acetal (Formula XXXII: $C_pH_{2p}$ is a valence bond with attachment in the meta position, $R_5$ and $R_6$ taken together are $-CH_2-C(CH_3)_2-CH_2-$, $R_{18}$ is

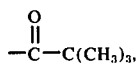

and ~ is endo)

Refer to Chart A, step (c).

(I). There is first prepared the formula-XXXI diol, namely 2-exo-(m-hydroxybenzyl)-3-exo-hydroxy-bicyclo-[3.1.0]-hexane-6-endo-carboxaldehyde neopentyl glycol acetal. A solution of the formula LIV product of Example 13 (17.97 g.) in 200 ml. of menthanol is treated with a solution of potassium carbonate (6.0 g.) in 65 ml. of water at 25° C. for 1 hr. The mixture is then concentrated under reduced pressure, diluted with 500 ml. of ice and water, and acidified to pH 5–6 with 1M. aqueous potassium hydrogen sulfate. The solution is saturated with sodium chloride and extracted with 800 ml. of chloroform. The organic phase is washed with brine, dried over sodium sulfate, and concentrated under reduced pressure to give the formula-XXXI diol, 17.83 g.

(II) A solution of the above diol (17.83 g.) in 150 ml. of pyridine is treated with pivaloyl chloride (17.75 ml.) following the procedure of Example 3-(II) to yield the title compound, 17.92 g., having the same properties as reported above.

EXAMPLE 15

2-Exo-{m[(carbomethoxy)methoxy]benzyl}-3-exo-(pivaloyloxy)-6-endo-(cis-1-heptenyl)-bicyclo[3.1.0-]hexane (Formula LVII: $C_pH_{2p}$ is a valence bond with attachment in the meta position, G is pentyl, $R_1$ is methyl, $R_3$ is hydrogen, $R_{18}$ is

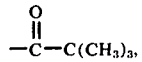

and ~ is endo)

Refer to Chart D, steps (d) and (e).

(I) There is first prepared the formula-LVI compound, namely 2-exo-(m-hydroxybenzyl)-3-exo-(pivaloloxy)-6-endo-(cis-1-heptenyl)-bicyclo[3.1.0-]hexane. A solution of the formula-LV (XXII of Chart A) compound, namely 2-exo-[m-(pivaloyloxy)benzyl]-3-exo-(pivaloyloxy)-6-endo-(cis-1-heptenyl)-bicyclo[3.1.0]hexane (Example 6(I), 1.42 g.) in 30 ml. of methanol and 2 ml. of water is treated with potassium carbonate (1.0 g.) at 25° C. for 3.5 hr. The mixture is concentrated under reduced pressure, diluted with 100 ml. of saturated aqueous potassium hydrogen sulfate and extracted with ethyl acetate. The organic phase is washed with brine, dried over sodium sulfate, and concentrated to give the formula-LVI compound, 1.20 g., having $R_f$ 0.69 (TLC on silica gel in 25% ethyl acetate in isomeric hexanes).

(II) A solution of the above formula-LVI compound, 1.20 g., in 10 ml. of 1,2-dimethoxyethane and treated with methyl bromoacetate (0.72 g.) and 0.15 g. of 57% sodium hydride dispersion. After standing 1.5 hr. at 25° C., the mixture is diluted with 180 ml. of 1.2 N. aqueous hydrochloric acid and extracted with ethyl acetate. The organic phase is washed with brine, dried over sodium sulfate and concentrated to give the formula-LVII title compound, 1.57 g. An analytical sample is obtained by subjecting the product to silica gel chromatography: $R_f$ 0.27 (TLC on silica gel in 10% ethyl acetate in isomeric hexanes); NMR peaks at 0.87, 1.18, 3.72, 4.55, 4.48–5.88, and 6.50–7.38 δ.

Following the procedures of Example 15(II) but replacing methyl bromoacetate with a haloacetate within the scope of $Cl-CH_2-COOCH_3$
$Br-CH_2-COOC_2H_5$
$Cl-CH_2-COOC_8H_{17}(n)$
$I-CH_2-COOCH_2C_6H_5$
$Cl-CH_2-COO(m-Cl-C_6H_4)$ there are obtained the corresponding formula-LVII compounds wherein $R_1$ is respectively methyl, ethyl, n-octyl, benzyl, and m-chlorophenyl.

Likewise following the procedures of Example 15(II) with each of the formula-LV (XXII of Chart A) compounds disclosed following Example 6 and using each of the haloacetates specifically identified above, there are obtained the corresponding formula-LVII compounds.

EXAMPLE 16 dl-8-{m-[2-(Methoxycarbonyl)ethyl]phenyl}-7-oxa-tricyclo[4.2.0.0$^{2,4}$]octane-6-endocarboxaldehyde Neopentyl Glycol Acetal (Formula LXIII wherein $R_5$ and $R_6$ taken together are $-CH_2-C(CH_3)_2-CH_2-$, $R_{19}$ is methyl, and ~ is éndo)

Refer to Chart E, step (a). A solution of racemic bicyclo(3.1.0)hex-2-ene-6-endo-carboxaldehyde neopentyl glycol acetal (corresponding to the optically active formula-XXX compound of Example 1, 5.82 g.) and the formula-LXXXI (m-formylphenyl) propionate, methyl ester (Preparation 6, 0.96 g.) in sufficient benzene to bring to a volume of 30 ml. is charged to a Pyrex photolysis vessel equipped with an immersible water-cooled cold-finger and fritted gas inlet tube. Dissolved oxygen is removed by bubbling nitrogen through the solution. The mixture is then irradiated at 350 nm. with a Rayonet Type RS Preparative Photochemical Reacter (The Southern New England Ultraviolet Co., Middletown, Conn.) equipped with six RUL 3500 A lamps. After 17 hr. the photolysate is concentrated under reduced pressure to an oil, which is subjected to silica gel chromatography. Elution with 10–75% ethyl acetate in Skellysolve B (mixture of isomeric hexanes) and finally ethyl acetate yields separate fractions of the recovered starting materials and the formula-LXIII title compound, an oil, 0.73 g., having NMR peaks at 0.67, 1.18, 3.65, 4.97-5.55, and 6.93-7.57 δ; mass spectral peaks at 386, 385, 115, 108, 84, 79, 69, 59, 45, 43, 41, and 29; infrared absorption bands at 3020, 2940, 2860, 1735, 1605, 1590, 1470, 1435, 1395, 1360, 1290, 1230, 1195, 1160, 1110, 1060, 1020, 1005, 985, 930, 915, 835, 785 and 705 cm$^{-1}$; and $R_f$ 0.18 (TLC on silica gel in ethyl acetate-Skellysolve B(25:75)).

EXAMPLE 17 dl-2-Exo-{m-[2-(methoxycarbonyl)ethyl]-benzyl}-3-exo-(pivaloyloxy)-bicyclo-[3.1.0]hexane-6-endo-carboxaldehyde Neopentyl Glycol Acetal (Formula LXV wherein $R_5$ and $R_6$ taken together are —$CH_2$—$C(CH_3)_2$—$CH_2$—, $R_{18}$ is pivaloyl, $R_{19}$ is methyl and ~ is endo)

(I). Refer to Chart E, steps (b) and (c). A mixture of the formula-LXIII oxetane (Example 16, 0.36 g., previously stirred with Raney Nickel catalyst and filtered), 10 ml. of ethyl acetate, 5 ml. of ethanol, and 0.25 g. of 10% palladium on charcoal is subjected to hydrogenation at one atmosphere at 25° C. unitl one molar equivalent has been absorbed. The mixture is filtered and concentrated to the formula LXVI compound, a colorless oil having $R_f$ 0.29 (TLC on silica gel plate in ethyl acetate-Skellysolve B (50:50)).

(II). The product of part (I) is dissolved in 10 ml. of pyridine and treated with 0.35 ml. of pivaloyl chloride for 2 days at about 25° C. The reaction mixture is mixed with 100 ml. of water, 200 ml. of diethyl ether, and saturated aqueous copper (II) sulfate. The ether extract is washed with water, saturated aqueous sodium bicarbonate, and brine, and dried over magnesium sulfate. Concentration under reduced pressure yields an oil, 0.56 g., which after silica gel chromatography (eluting with first dichloromethane and then ethyl acetate-Skellysolve B (35:65)) yields the title compound as an oil, 0.48 g., having $R_f$ 0.42 (TLC on silica gel in ethyl acetate-Skellysolve B (25:75)); and NMR peaks at 0.72, 1.21, 3.65, 4.18 (doublet, J = 6.5 $H_z$), 5.00, and 6.80-7.40 δ.

EXAMPLE 18 dl-2-Exo-{m-[2-(methoxycarbonyl)ethyl]-benzyl}-3-exo-(pivaloyloxy)bicyclo[3.1.0]hexane-6-endo-carboxaldehyde (Formula LXVII, wherein $R_{16}$ is pivaloyl, $R_{20}$ is methyl and ~ is endo)

Refer to Chart E, step (d). The formula-LXV acetal, i.e. dl-2-exo-{m-[2-(methoxycarbonyl)ethyl]benzyl}-3-exo-(pivaloyloxy)bicyclo[3.1.0]hexane-6-endo-carboxaldehyde neopentyl glycol acetal (Example 17, 0.48 g.) is treated at 0° C. with 25 ml. of 88% formic acid for 2.75 hr. The mixture is diluted with 500 ml. of brine, and extracted with 200 ml. of ethyl acetate. The organic phase is washed with brine and saturated aqueous sodium bicarbonate, and dried over sodium sulfate. Concentration under reduced pressure yields an oil, which when subjected to silica gel chromatography (eluting with 10-30% ethyl acetate-Skellysolve B) yields the title compound as an oil, 0.25 g. having NMR peaks at 1.22, 3.67, 5.15-5.57, 6.87-7.42, and 9.67 δ(doublet, J = 4 $H_z$); and $R_f$ 0.26 (TLC on silica gel in ethyl acetate-Skellysolve B (25:75)).

EXAMPLE 19 dl-2-Exo-{m-[2-(methoxycarbonyl)ethyl]-benzyl}-3-exo-(pivaloyloxy)-6-endo-(cis-1-heptenyl)bicyclo[3.1.0]hexane (Formula LXVIII, wherein $R_3$ is hydrogen, $R_{16}$ is pivaloyl, $R_{20}$ is methyl, and ~ is endo)

Refer to Chart E step (e). The formula-LXVII aldehyde, i.e. dl-2-exo-{m-[2-(methoxycarbonyl)ethyl]-benzyl}-3-exo-(pivaloloxy)bicyclo[3.1.0]hexane-6-endo-carboxaldehyde (Example 18, 0.25 g.) in 5 ml. of benzene is added to the Wittig ylid reagent (prepared in 15 ml. of benzene from nhexyltriphenylphosphonium bromide (0.60 g.) and n-butylithium (0.52 ml. of 2.32 M. solution in hexane) at about 25° C for 0.5 hr. and using the supernatant). After 0.5 hr. there is added 1.0 ml. of acetone and the mixture stirred at 25° C. for 10 min. The mixture is diluted with 250 ml. of brine and extracted with 200 ml. of ethyl acetate. The organic phase is washed with brine and dried over magnesium sulfate. Concentration under reduced pressure yields an oil, 0.54 g., which when subjected to silica gel chromatography (eluting with dichloromethane) yields the title compound as an oil, 0.20 g. having $R_f$ 0.66 (TLC on silica gel in 25% ethyl acetate-Skellysolve B) and NMR peaks at 0.88, 1.19, 1.25, 3.68, 4.68-6.03 and 6.86-7.43 δ.

Thereafter, following the procedures of Chart F, the product of Example 19 is converted to the racemic glycol corresponding to formula LXXIV wherein $R_1$ is methyl and thence to dl-4,5,6-trinor-3,7-inter-m-phenylene-PGF$_{1\alpha}$, methyl ester, corresponding to formula LXXV, a useful compound.

EXAMPLE 20 dl-2-Exo-[m-(2-carboxyethyl)benzyl]-3-exo-hydroxy-6-endo-(cis-1-heptenyl)-bicyclo[3.1.0]hexane (Formula LXIX wherein $R_1$ and $R_3$ are hydrogen, and ~ is endo); and dl-2-Exo-{m-[2-(methoxycarbonyl)ethyl]benzyl}-3-exo-hydroxy-6-endo-(cis-1-heptenyl)-bicyclo[3.1.0]hexane (Formula LXIX wherein $R_1$ is methyl, $R_3$ is hydrogen, and ~ is endo)

(I). Refer to Chart E, step (f). The formula-LXVIII diester, i.e. dl-2-exo-{m-[2-(methoxycarbonyl)ethyl)-benzyl}3-exo-(pivaloyloxy)-6-endo-(cis-1-heptenyl)-bicyclo[3.1.0]-hexane (Example 19, 0.20 g.) is treated in 5 ml. of methanol with 2.0 ml. of 25% sodium methoxide in methanol at about 25° C. for 15 hr., then at reflux for 4 hr. The reaction mixture is acidified with 2 ml. of glacial acetic acid and then concentrated under reduced pressure. The residue is taken up in 200 ml. of ethyl acetate, washed with brine and dried over sodium sulfate. Concentration under reduced pressure yields the formula-LXIX title compound wherein $R_1$ is hydrogen as a pale yellow oil.

(II). The product of step (I) above in methanol, is converted to the methyl ester with diazomethane at 25° C. for 3-5 min. washed in ethyl acetate solution with saturated aqueous sodium bicarbonate and brine and dried over sodium sulfate to the formula-LXIX title compound wherein $R_1$ is methyl, an oil, 0.18 g. having $R_f$ 0.20 (TLC on silica gel in 25% ethyl acetate-Skellysolve B).

EXAMPLE 21 dl-2-Exo-{m-[2-(methoxycarbonyl)ethyl]-benzyl}-6-endo-(cis-1-heptenyl)-bicyclo-[3.1.0]hexane-3-one (Formula LXX: $R_1$ is methyl, $R_3$ is hydrogen and $\sim$ is endo)

Refer to Chart E, step (g). The formula-LXIX hydroxy compound, i.e. dl-2-exo-{m-[2-(methoxycarbonyl)ethyl]benzyl}-3-exo-hydroxy-6-endo-(cis-1-heptenyl)-bicyclo[3.1.0]hexane is oxidized as follows. The formula-LXIX compound wherein $R_1$ is methyl (Example 20, 0.18 g.) in dichloromethane is added to a solution of Collins reagent (prepared from pyridine (0.48 g.) and chromium trioxide (0.3 g.) in 10 ml. dichloromethane at about 25° C. for 20 min.). The reaction mixture is then shaken with a mixture of 100 ml. of diethyl ether and 300 ml. of brine. The organic phase is shaken with a mixture of ice and 1N. aqueous sodium hydroxide, then washed with water, saturated aqueous copper (II) sulfate, water, and brine, and dried over sodium sulfate. Concentration under reduced pressure yields a pale yellow oil, 0.20 g., which when subjected to silica gel chromatography (eluting with 5–10% ethyl acetate-Skellysolve B) yields the title compound, a colorless oil, 0.07 g., having $R_f$ 0.61 (TLC on silica gel in 25% ethyl acetate-Skellysolve B); NMR peaks at 0.88, 3,67, 4.68-5.18, 5.27-5.97, and 6.95-7.35 δ; infrared absorption bands at 2960, 2920, 2850, 1740, 1610, 1590, 1490, 1440, 1365, 1260, 1240, 1195, 1155, 1060, 785, and 705 cm$^{-1}$; and mass spectral peaks at 368, 350, 337, 326, 191, and 177.

Thereafter, following the procedure of Chart E, the product of Example 21 is converted to the racemic glycol corresponding to formula LXXI wherein $R_1$ is methyl and thence to dl-4,5,6-trinor-3,7-inter-m-phenylene-PGE$_1$, methyl ester, corresponding to formula LXXII, a useful compound.

Following the procedures of Examples 16–21 but using the optically active form of starting material XXX (from Example 1), there are obtained the corresponding optically active intermediates and final products.

I claim:

1. An optically active compound of the formula

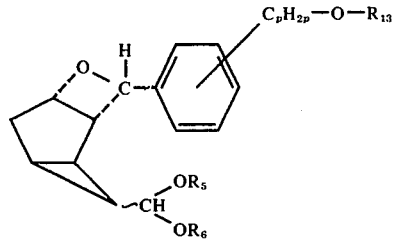

or a racemic mixture of that compound and the enantiomer thereof, wherein $C_pH_{2p}$ represents a valence bond or alkylene of one to 4 carbon atoms, inclusive, with one or 2 carbon atoms in the chain between the phenylene ring and —O—; wherein $R_5$ and $R_6$ are the group represented by the formula

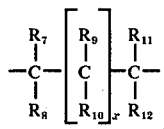

wherein $R_7$, $R_8$, $R_9$, $R_{10}$, $R_{11}$, and $R_{12}$ are hydrogen, alkyl of one to 4 carbon atoms, inclusive, or phenyl, with the proviso that not more than one of the R's phenyl and the total number of carbon atoms is from 2 to 10, inclusive; and $x$ is zero or one; wherein $R_{13}$ is carboxyacyl of the formula

wherein $R_{14}$ is hydrogen, alkyl of one to 19 carbon atoms, inclusive, or aralkyl of 7 to 12 carbon atoms, inclusive, wherein alkyl or aralkyl are substituted with zero to 3 halo atoms; and wherein $\sim$ indicates attachment to the cyclopropane ring in endo or exo configuration.

2. A compound according to claim 1 wherein $R_5$ and $R_6$ taken together are —CH$_2$—C(CH$_3$)$_2$CH$_2$—and $\sim$ is endo.

3. A compound according to claim 2 wherein $C_pH_{2p}$ is a valence bond with attachment in the meta position.

4. A compound according to claim 3 wherein $R_{13}$ is

5. A compound according to claim 3 wherein $R_{13}$ is

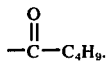

6. A compound according to claim 3 wherein $R_{13}$ is

* * * * *

UNITED STATES PATENT AND TRADEMARK OFFICE
CERTIFICATE OF CORRECTION

PATENT NO. : 3,997,566
DATED : 14 December 1976
INVENTOR(S) : Douglas R. Morton, Jr.

It is certified that error appears in the above-identified patent and that said Letters Patent are hereby corrected as shown below:

Cover page, "TRICYCLIC PROSTAGLANDIN" should read -- TRICYCLIC PROSTAGLANDIN INTERMEDIATES --.

Column 1, line 35, the formula should appear as follows:

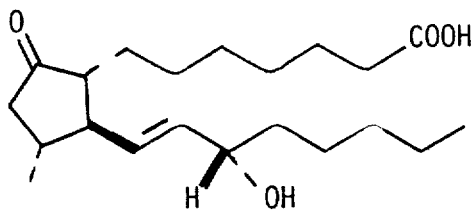

Column 1, line 47, the formula should appear as follows:

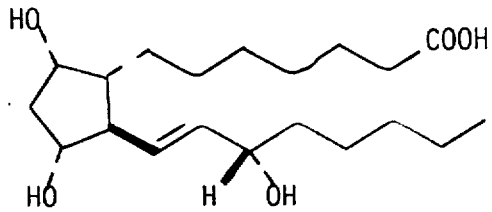

Column 4, line 2, the formula should appear as follows:

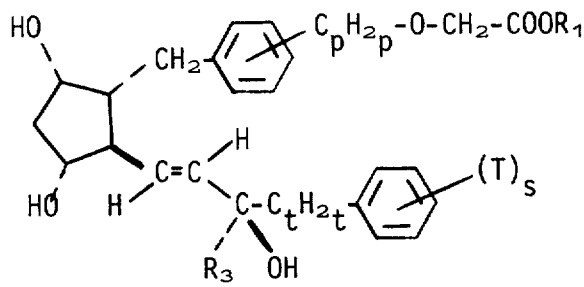

UNITED STATES PATENT AND TRADEMARK OFFICE
CERTIFICATE OF CORRECTION

PATENT NO. : 3,997,566

DATED : 14 December 1976

INVENTOR(S) : Douglas R. Morton, Jr.

It is certified that error appears in the above-identified patent and that said Letters Patent are hereby corrected as shown below:

Column 4, line 35, the formula should appear as follows:

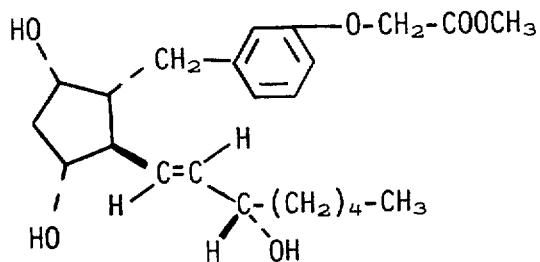

Column 5, line 12, "proceding" should read -- preceding --.
Column 9, line 33, "-PGF$_1$," should read -- -PGE$_1$, --.
Column 11, line 26, the formula should appear as follows:

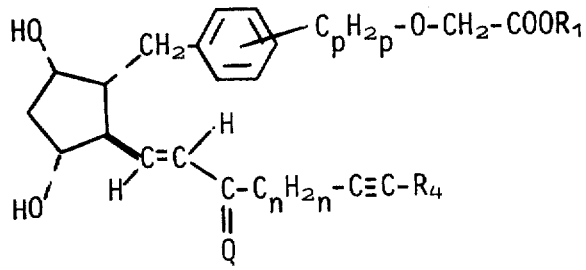

Column 13, line 54, "there if" should read -- there is --.
Column 14, line 21, "R$_3$m and" should read -- R$_3$, and --.
Column 21, Formula XXXVI should appear as follows:

UNITED STATES PATENT AND TRADEMARK OFFICE
CERTIFICATE OF CORRECTION

PATENT NO. : 3,997,566  
DATED : 14 December 1976  
INVENTOR(S) : Douglas R. Morton, Jr.

Page 3 of 3

It is certified that error appears in the above-identified patent and that said Letters Patent are hereby corrected as shown below:

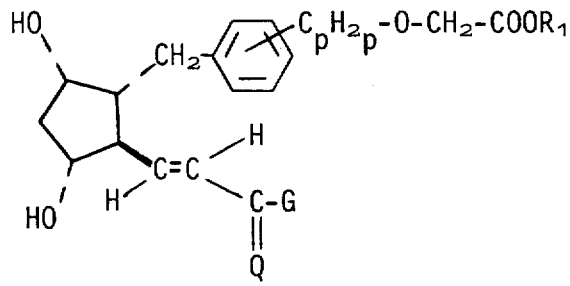

Column 27, line 13, "ester" should read -- ether --.  
Column 42, line 51, "PGF$_1$-type" should read -- PGF$_{1\alpha}$-type --.  
Column 45, line 61, "13.1.0]hex-" should read -- 1-Bicyclo[3.1.0]hex- --.  
Column 48, line 20, "sulphate" should read -- sulfate --.  
Column 51, line 7, "-(CH$_2$)$_2$-C≡C-C$_2$H$_5$" should read --       -- (appears twice, once on page 50).  
Column 51, line 9, "-CH$_2$-CH(CH$_3$)-C≡C-C$_2$H$_5$ or" should read-- -CH$_2$-C(CH$_3$)$_2$-C≡C-C$_2$H$_5$ or --.  
Column 53, line 41, "with one" should read -- with each one --.  
Column 60, line 25, "R's phenyl" should read -- R's is phenyl --.

Signed and Sealed this

Eighteenth Day of August 1981

[SEAL]

Attest:

GERALD J. MOSSINGHOFF

Attesting Officer    Commissioner of Patents and Trademarks